US008785605B2

(12) United States Patent
Almagro et al.

(10) Patent No.: US 8,785,605 B2
(45) Date of Patent: Jul. 22, 2014

(54) HUMANIZED IL-25 ANTIBODIES

(75) Inventors: Juan Carlos Almagro, Radnor, PA (US); Patrick Branigan, Radnor, PA (US); Colleen Kane, Radnor, PA (US); William Strohl, Radnor, PA (US); Susann Taudte, Radnor, PA (US); Mark Tornetta, Radnor, PA (US); John Wheeler, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 13 days.

(21) Appl. No.: 13/075,241

(22) Filed: Mar. 30, 2011

(65) Prior Publication Data
US 2011/0318353 A1 Dec. 29, 2011

Related U.S. Application Data

(60) Provisional application No. 61/341,458, filed on Mar. 30, 2010, provisional application No. 61/319,260, filed on Mar. 31, 2010.

(51) Int. Cl.
C07K 16/24 (2006.01)
A61K 9/19 (2006.01)
A61K 39/395 (2006.01)

(52) U.S. Cl.
USPC ............... 530/388.23; 530/387.3; 530/387.9; 530/861; 530/866; 424/145.1; 424/489

(58) Field of Classification Search
None
See application file for complete search history.

(56) References Cited

U.S. PATENT DOCUMENTS

| | | | |
|---|---|---|---|
| 6,562,578 B1 | 5/2003 | Gorman et al. | |
| 6,884,879 B1 * | 4/2005 | Baca et al. | 536/23.53 |
| 7,592,426 B2 * | 9/2009 | Ebel et al. | 530/387.3 |
| 8,206,717 B2 | 6/2012 | McKenzie et al. | |
| 2002/0155114 A1 | 10/2002 | Marks et al. | |
| 2003/0008815 A1 | 1/2003 | Chen et al. | |
| 2006/0078966 A1 | 4/2006 | Medlock et al. | |
| 2006/0204506 A1 | 9/2006 | Ebel et al. | |
| 2007/0280950 A1 | 12/2007 | Okabe et al. | |
| 2009/0148435 A1 | 6/2009 | Lebreton et al. | |
| 2009/0263401 A1 | 10/2009 | Hurst et al. | |

FOREIGN PATENT DOCUMENTS

| | | |
|---|---|---|
| EP | 2 163 625 A1 | 3/2010 |
| WO | WO 92/01047 A1 | 1/1992 |
| WO | WO 2006/094384 A1 | 9/2006 |
| WO | WO 2007/044450 A2 | 4/2007 |
| WO | WO 2008/129263 A1 | 10/2008 |
| WO | WO 2009/136976 A1 | 1/2009 |
| WO | WO 2010/038155 A2 | 4/2010 |

OTHER PUBLICATIONS

AWO22746, GENESEQ™ database, Thomson Reuters, Philadelphia, USA, Accession No. AZM72167, Sep. 14, 2012.*
AYJ86549, GENESEQ™ database, Thomson Reuters, Philadelphia, USA, Accession No. AYJ86549, Sep. 14, 2012.*
Boder et al. Directed evolution of antibody fragments with monovalent femtomolar antigen-binding affinity. Proc Natl Acad Sci U S A Sep. 26, 2000;97(20):10701-5.*
Rudikoff et al. Single amino acid substitution altering antigen-binding specificity. Proc Natl Acad Sci U S A. Mar. 1982;79(6):1979-83.*
De Pascalis et al. Grafting of "abbreviated" complementarity-determining regions containing specificity-determining residues essential for ligand contact to engineer a less immunogenic humanized monoclonal antibody. J Immunol. Sep. 15, 2002;169(6):3076-84.*
Wu et al. Humanization of a murine monoclonal antibody by simultaneous optimization of framework and CDR residues. J Mol Biol. Nov. 19, 1999;294(1)151-62.*
Almagro, et al., "Humanization of antibodies," Frontiers in Bioscience, 13, 1619-1633 (2008).
Angkasekwinai, et al., "Interleukin25 promotes the initiation of proallergic type 2 responses," The Journal of Experimental Medicine, 204(): 1509-1517 (2007).
Angkasekwinai, et al., "The Role of IL-25 in Airway Allergic Response," Journal of Allergy and Clinical Immunology, 119(1): S134, Abstract 530 (2007).
Ballantyne, et al., "Blocking IL-25 prevents airway hyperresponsiveness in allergic asthma," Journal of Allergy and Clinical Immunology, 120(6): 1324-1331 (2007).
Budelsky, et al., "Transgenic Mice Overexpressing Human IL-17E Exhibit an Asthma-Like Phenotype that is Exacerbated in an Ovalbumin-Induced Model of Asthma," Journal of Allergy and Clinical Immunology, 117(20: S253, Abstract 980 (2006).
Casset, et al., "A peptide mimetic of an anti-CD4 monoclonal antibody by retional design," Biochemical and Biophysical Research Communication, 307: 198-205 (2003).
Chen, et al., "Selection and Analysis of an Optimized Anti-VEGF Antibody: Crystal Structure of an Affinity-matured Fab in Complex with Antigen," Journal of Molecular Biology, 293: 865-881 (1999).
Dall'Acqua, et al., "Antibody humanization by framework shuffling," Methods, 36(1): 43-60 (2005).
Davies, et al., "Affinity improvement of single antibody VH domains: residues in all three hypervariable regions affect antigen binding," Immunotechnology, 2: 169-179 (1996).
Fallon, et al., "Identification of an interleukin (IL)-25-dependent cell population that provides IL-4, IL-5, and IL-13 at the onset of helminth expulsion," The Journal of Experimental Medicine, 203(4): 1105-116 (2006).
Fort, et al., "IL-25 Induces IL-4, IL-5, and IL-13 and Th2-Associates Pathologies In Vivo," Immunity, 15: 985-995 (2001).

(Continued)

*Primary Examiner* — David Romeo
(74) *Attorney, Agent, or Firm* — Kirk Baumeister

(57) ABSTRACT

The present invention relates to target binding members (e.g., antibodies) that bind a specified epitope of human IL-25. The invention also relates to target binding members (e.g., antibodies) that comprise one or more humanized antibody VL domain sequences and bind IL-25. The invention further relates to compositions comprising target binding members (e.g., antibodies) that bind IL-25, methods of producing such target binding members, and uses of such target binding members for the treatment or prevention of diseases and conditions (e.g., asthma, inflammatory bowel disease).

13 Claims, 19 Drawing Sheets

(56) References Cited

OTHER PUBLICATIONS

Holt, et al., Domain antibodies: proteins for therapy: TRENDS in Biotechnology, 21(11): 484-490 (2003).

Holm, et al., "Functional mapping and single chain construction of the anti-cytokeratin 8 monoclonal antibody TS1," Molecular Immunology, 44: 1075-1084 (2007).

Kawaguchi, et al., "IL-17 cytokine family," Journal of Allergy and Clinical Immunology, 114(6): 1265-1273 (2004).

Lazar, et al., "A molecular immunology approach to antibody humanization and functional optimization," Molecular Immunology, 44(8): 1986-1998 (2007).

Létuvé, et al., "IL-17E upregulates the expression of proinflammatory cytokines in lung fibroblasts," Journal of Allergy and Clinical Immunology, 117(3): 590-596 (2006).

Little, et al., "Of mice and men: hybridoma and recombinant antibodies," Immunology Today, 21(8): 364-370 (2000).

MacCallum, et al., "Antibody-antigen Interactions: Contact Analysis and Binding Site Topography," Journal of Molecular Biology, 262: 732-745 (1996).

Marks, et al., "By-passing Immunization—Human Antibodies from V-gene Libraries Displayed on Phage," Journal of Molecular Biology, 22: 581-597 (1991).

Owyang, et al., "Interleukin 25 regulates type 2 cytokine-dependent immunity and limits chronic inflammation in the gastrointestinal tract," The Journal of Experimental Medicine, 203(4): 843-849 (2006).

Carayannopoulos, et al., "Immunoglobulins Structure and Function," Fundamental Immunology, Third Edition, Chapter 9: 283-314 (1993).

R&D Systems, "Monoclonal Anti-Human IL-17E Antibody," Mar. 2007. Retrieved from Internet URL: http://www.rndsystems.com/pdf/mab1258.pdf. Retrieved on Aug. 19, 2011.

Sharkhuu, et al., "Mechanism of interleukin-25 (IL-17E)-induced pulmonary inflammation and airways hyper-reactivity," Clinical and Experimental Allergy, 36: 1575-1583 (2006).

Tamachi, et al., "IL-25 enhances allergic airway inflammation by amplifying a $T_H2$ cell-dependent pathway in mice," Journal of Allergy and Clinical Immunology, 118: 606-614 (2006).

Vajdos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).

PCT International Search Report dated Jun. 21, 2011.

Brown, et al., Tolerance of single, but not multiple, amino acid replacements in antibody VH CDR 2: a means of minimizing B cell wastage from somatic hypermutation? The Journal of Immunology, 156 (9): 3285-3291 (1996).

Giusti, et al., "Somatic diversification of S107 from an antiphosphocholine to an anti-DNA autoantibody is due to a single base change in its heavy chain variable region," Proceedings of the National Academy of Science USA, 84: 2926-2930 (1987).

Kussie, et al., "A Single Engineered Amino Add Substitution Changes Antibody Fine Specificity," Journal of Immunology, 152: 146-162 (1994).

Liu, et al., "Fine mapping of the antigen-antibody interaction of scFv215, a recombinant antibody inhibiting RNA polymerase II from *Drosophila melanogaster*," Journal of Molecular Recognition, 12: 103-111 (1999).

Maynard, et al., "Antibody Engineering," Annual Review of Biomedical Engineering, 2: 339-376 (2000).

Pini, et al., "Design and Use of a Phage Display Library: Human antibodies with Subnanomolar Affinity Against a marker of Angiogenesis Eluted from a Two-Dimensional Gel," the Journal of Biological Chemistry, 273 (34): 21769-21776 (1993).

Rudikoff, et al., "Single amino acid substitution altering antigen-binding specificity," proceedings of the National Academy of Science USA, 79: 1979-1983 (1983).

Schildbach, et al., "Contribution of a single heavy chain residue to specificity of an anti-digoxin monoclonal antibody," Protein Science, 3: 737-749 (1994).

Schildbach, et al., "Heavy Chain Position 50 is a Determinant of Affinity and Specificity for the anti-digoxin Antibody 2," The Journal of Biological Chemistry, 268 (29): 21739-21747 (1993).

Wang, et al., "The IL-17 Cytokine family and their role in allergy inflammation," Current Opinion in Immunology, 20 (6): 697-702 (2008).

Xiang, et al., "Study of B72.3 combining sites by molecular modeling and site-directed mutagenesis," Protein Engineering, 13 (5): 339-344 (2000).

\* cited by examiner

FIG. 1

GATGACCCAGTCTCCATCCTCCCTGTCTGCATCTGTAG
GAGACAGAGTCACCATCACTTGCAGTGCATCCCAGGGC
ATTAGCAATTATCTGAATTGGTATCAGCAGAAACCAGGG
AAAGTTCCTAAACTCCTGATCTATTACACATCAAGTTTAC
ACTCAGGGGTCCCATCTCGGTTCAGCGGCAGTGGATCT
GGGACAGATTTCACTCTCACCATCAGCAGCCTGCAGCC
TGAAGATGTTGCAACTTATTACTGTCAGCAGTATAGCAA
GCTGCCGTACACGTTTGGCCAGGGGACCAAGCTGGAG
ATCAAA (SEQ ID NO:1)

DIQMTQSPSSLSASVGDRVTITC<u>SASQGISNYLN</u>WYQQKP
GKVPKLLIY<u>YTSSLHS</u>GVPSRFSGSGSGTDFTLTISSLQPE
DVATYYC<u>QQYSKLPYT</u>FGQGTKLEIK (SEQ ID NO:2)

FIG. 2

GAGGTGCAGCTGGTCGAGAGCGGAGCCGAGGT
GAAGAAGCCAGGCGCCAGCGTCAAGGTGTCCTG
CAAGGCCAGCGGCTACAGCTTCTCCGGCTACAC
CATGAACTGGGTGCGGCAGGCCCAGGCCAGAG
GCTGGAATGGATGGGCCTGATCAACCCCTACAAC
GGCGGCACCAGCTACAACCAGAACTTCAAGGGC
AGGGTGACACTGACCGTGGATACCAGCGCCAGC
ACCGCCTACCTGGAACTGAACAGCCTGAGAAGC
GAGGACACCGGCGTGTACTACTGCGCCAGAGAG
GACTACGACGGCTACCTGTACTTCGCCATGGACT
ACTGGGGCCAGGGCACCCTGGTGACCGTGAGC
(SEQ ID NO:3)

EVQLVESGAEVKKPGASVKVSCKASGYSFS<u>GYTM
N</u>WVRQAPGQRLEWMG<u>LINPYNGGTSYNQNFKGR</u>
VTLTVDTSASTAYLELNSLRSEDTGVYYCAR<u>EDYDG
YLYFAMDY</u>WGQGTLVTVS (SEQ ID NO:4)

FIG. 3

| | LCDR1 | | | | | | | | | | | LCDR3 | | | | | | | | | | HCDR3 | | | | | | | | | | | | | KD (pM) Biacore For 7200 sec diss | Receptor inhibition IC50, pM | Cellular Inhibition |
|---|---|---|---|---|---|---|---|---|---|---|---|---|---|---|---|---|---|---|---|---|---|---|---|---|---|---|---|---|---|---|---|---|---|---|---|---|---|
| | S | A | S | Q | G | I | S | N | Y | L | N | Q | Q | Y | S | K | L | P | Y | T | F | E | D | Y | D | G | Y | L | Y | F | A | M | D | Y | | Panel A/B | fold change |
| huDDG91 | | | | | | | | | | | | | | | | | | | | | | | | | | | | | | | | | | | | | |
| I25M6 | - | - | - | - | - | - | - | - | - | - | - | - | - | - | - | L | A | F | - | - | - | - | - | F | - | - | - | - | - | - | - | - | - | - | 53 | 12 | 4 |
| I25M10 | - | - | - | - | - | - | - | - | - | - | - | - | - | - | - | L | A | F | - | - | - | - | - | F | - | S | W | T | F | - | - | - | - | - | 36 | 14 | 5 |
| I25M11 | - | - | - | A | S | F | - | - | - | - | - | - | - | - | - | S | F | - | - | - | - | - | - | F | - | S | W | T | F | - | - | - | - | - | 57 | 14 | 5 |
| I25M20 | - | - | - | - | - | - | - | - | - | - | - | - | - | - | - | L | A | F | - | - | - | - | - | Y | - | S | W | T | F | - | - | - | - | - | 45 | 13 | 20 |
| I25M32 | - | - | - | N | E | - | - | - | - | - | - | - | - | - | - | I | N | F | - | - | - | - | - | Y | - | S | W | T | Y | - | - | - | - | - | 87 | 11 | 4 |
| I25M28 | - | - | - | - | - | - | - | - | - | - | - | - | - | - | - | L | A | F | - | - | - | - | - | F | - | S | W | T | Y | - | - | - | - | - | 19 | 14 | 16 |
| I25M30 | - | - | - | H | W | N | - | - | - | - | - | F | N | S | F | - | - | - | - | - | - | - | - | F | - | S | W | T | Y | - | - | - | - | - | 44 | 20 | 3 |
| I25M31 | - | - | - | - | - | - | - | - | - | - | - | - | - | - | - | - | - | - | - | - | - | - | - | F | - | S | W | T | Y | - | - | - | - | - | 40 | 18 | 12 |
| I25M34 | - | - | - | N | E | - | - | - | - | - | - | - | - | - | - | I | N | F | - | - | - | - | - | F | - | S | W | T | Y | - | - | - | - | - | 64 | 13 | 7 |
| IL-17BR | | | | | | | | | | | | | | | | | | | | | | | | | | | | | | | | | | | 17 | 63 | 1 |
| R71V G1 | | | | | | | | | | | | | | | | | | | | | | | | | | | | | | | | | | | 194 | 45.2-64.3 | |
| R71V G1 | | | | | | | | | | | | | | | | | | | | | | | | | | | | | | | | | | | 136 | | |

Fig 4A.

M6 Light Chain (LC) Amino Acid Sequence

DIQMTQSPSSLSASVGDRVTITCSASQGISNYLNWYQQKP
GKVPKLLIYYTSSLHSGVPSRFSGSGSGTDFTLTISSLQP
EDVATYYCQQYLAFPYTFGQGTKLEIKRTVAAPSVFIFPP
SDEQLKSGTASVVCLLNNFYPREAKVQWKVDNALQSGNSQ
ESVTEQDSKDSTYSLSSTLTLSKADYEKHKVYACEVTHQG
LSSPVTKSFNRGEC (SEQ ID NO:5)

LC CDR 1: SASQGISNYLN (SEQ ID NO:6)

LC CDR 2: YTSSLHS (SEQ ID NO:7)

LC CDR 3: QQYLAFPYTF (SEQ ID NO:8)

FIG. 4B

M6 Heavy Chain (HC) Amino Acid Sequence

EVQLVESGAEVKKPGASVKVSCKASGYSFSGYTMNWVRQ
APGQRLEWMGLINPYNGGTSYNQNFKGRVTLTVDTSASTA
YLELNSLRSEDTGVYYCAREDYDGYLYFAMDYWGQGTLVT
VSSASTKGPSVFPLAPSSKSTSGGTAALGCLVKDYFPEPVT
VSWNSGALTSGVHTFPAVLQSSGLYSLSSVVTVPSSSLGT
QTYICNVNHKPSNTKVDKKVEPKSCDKTHTCPPCPAPELL
GGPSVFLFPPKPKDTLMISRTPEVTCVVVDVSHEDPEVKFN
WYVDGVEVHNAKTKPREEQYNSTYRVVSVLTVLHQDWLN
GKEYKCKVSNKALPAPIEKTISKAKGQPREPQVYTLPPSRD
ELTKNQVSLTCLVKGFYPSDIAVEWESNGQPENNYKTTPPV
LDSDGSFFLYSKLTVDKSRWQQGNVFSCSVMHEALHNHYT
QKSLSLSPGK (SEQ ID NO:9)

HC CDR 1: GYTMN (SEQ ID NO:10)

HC CDR 2: LINPYNGGTSYNQNFKG (SEQ ID NO:11)

HC CDR 3: EDYDGYLYFAMDY (SEQ ID NO:12)

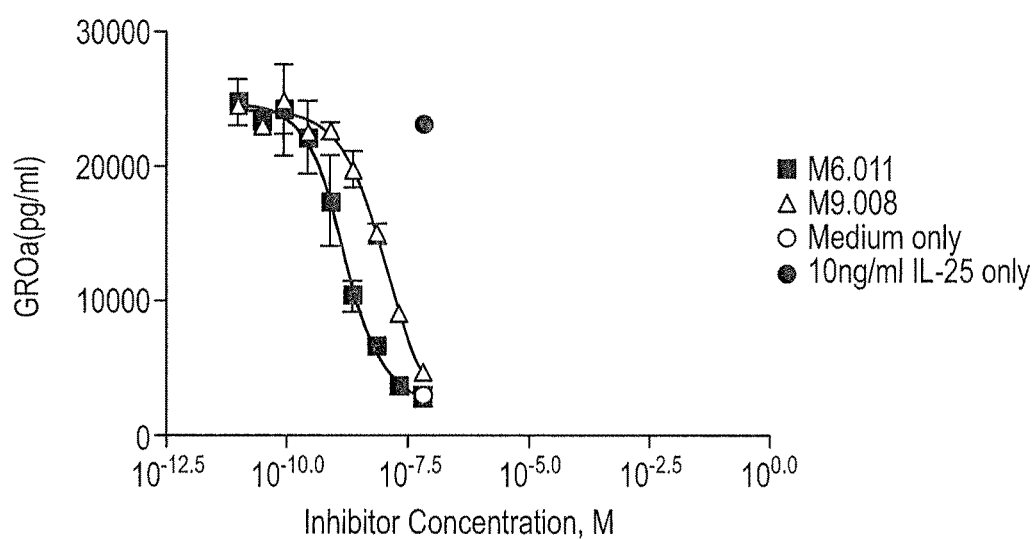

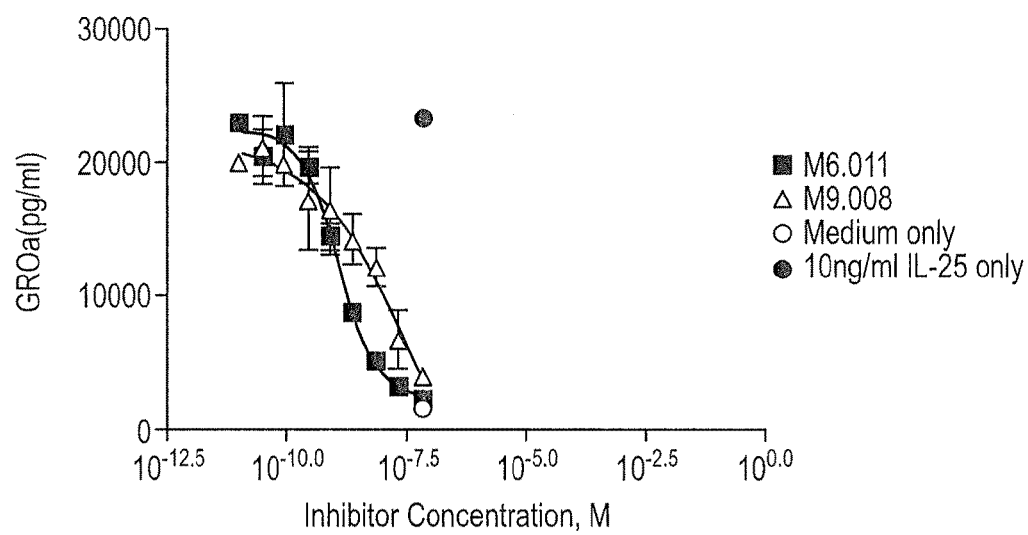

FIG. 7A

MYSHWPS[CC]PSKGQDTSEELLRWSTVPVPPLEPARPNAHPES[C]RASEDGPLNSRAISPWRYELDADLNRLPQDLYHAR (SEQ ID NO: 13)

*FIG. 7B*

CLCPHCVSLQTGSHHDPRGNSELLYHNQTVFYRRPCHGEKGTHKGYCLERRLYRWSLACVCVRPRVMG
80      90        100       110       120       130       140
                                                              (SEQ ID NO: 14)

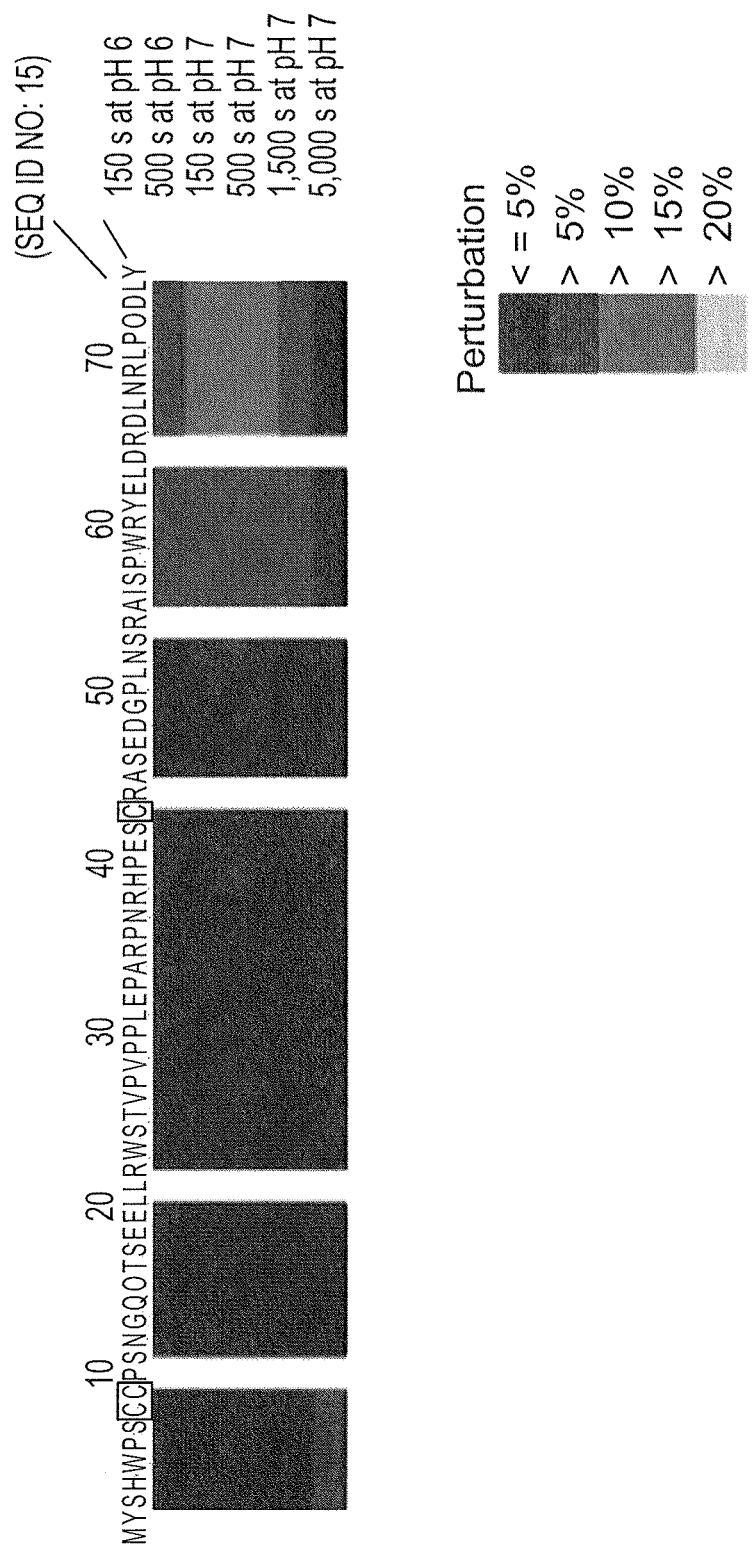

FIG. 10

MYSHWPSCCPSKGQDTSEELLRWSTVPVPP
LEPARPNRHPESCRASEDGPLNSRAISPWR
YELDRDLNRLPQDLYHARCLCPHCVSLQTG
SHMDPRGNSELLYHNQTVFYRRPCHGEKGT
HKGYCLERRLYRVSLACVCVRPRVMG (SEQ ID NO:17)

HUMANIZED IL-25 ANTIBODIES

CROSS-REFERENCE TO RELATED APPLICATIONS

This application claims priority to U.S. Provisional Ser. No. 61/341,458, filed 30 Mar. 2010 and U.S. Provisional Ser. No. 61/319,260, filed 31 Mar. 2010. The entire content of each of the aforesaid applications is incorporated herein by reference in their entireties.

BACKGROUND OF THE INVENTION

Interleukin-25 (IL-25), also known as IL-17E, is a cytokine that belongs to the IL-17 cytokine family and is secreted by type 2 helper T cells (Th2) and mast cells. IL-25 induces the production of other cytokines, including IL-4, IL-5 and IL-13, in multiple tissues and stimulates the expansion of eosinophils.

IL-25 has been implicated in chronic inflammation associated with the gastrointestinal tract and the IL-25 gene has been identified in a chromosomal region associated with autoimmune diseases of the gut, such as inflammatory bowel disease (IBD). Conventional therapies for treatment of IBD involve either antibiotics or steroid-derived drugs; however these are not currently successful in inducing or maintaining clinical remission in patients.

IL-25 has also been shown to be upregulated in samples from patients with asthma, a condition estimated to affect more than 300 million people worldwide, suggesting that overexpression of this cytokine contributes to the pathology of asthma and related conditions.

Thus, there is a need for effective antagonists of IL-25 that are useful in the treatment of diseases and conditions characterized by IL-25 overexpression, including asthma and inflammatory bowel disease.

SUMMARY OF THE INVENTION

The present invention relates to target binding members, including antibodies and binding fragments thereof, directed to interleukin 25 (IL-25).

The present invention further relates to variants of RH2.5_R71V, a humanized (CDR-grafted) version of the murine 2C3 antibody, also referred to herein using the terms "huDDG91" and "M9." One such variant is referred to herein as the "M6 antibody," or "M6." M6 exhibits a number of beneficial properties in vitro and in vivo, including, for example, enhanced binding affinity for IL-25 relative to the parent huDDG91 antibody, improved abilities to inhibit IL-25 receptor in receptor and cell-based assays relative to the parent huDDG91 antibody and other characteristics, such as high expression level, high solubility, lack of significant protein aggregation upon purification, and absence of undesired post-translational modifications, protein-protein interactions and oxidation upon purification.

In one embodiment, the invention relates to a target binding member that binds IL-25, wherein the target binding member binds one or more amino acid sequences selected from the group consisting of amino acid residues 46-63 of SEQ ID NO:17, amino acid residues 66-84 of SEQ ID NO:17 and amino acid residues 129-135 of SEQ ID NO:17. In a particular embodiment, the target binding member of the invention binds amino acid residues 56-63 of SEQ ID NO:17 and amino acid residues 66-74 of SEQ ID NO:17. In another embodiment, the target binding member comprises an antibody VL domain comprising a CDR3 having the amino acid sequence QQYLAFPYTF (SEQ ID NO:8).

In another embodiment, the invention relates to a target binding member that binds IL-25, wherein the target binding member comprises:
a) an antibody VL domain comprising a CDR1 having the amino acid sequence SASQGISNYLN (SEQ ID NO:6), a CDR2 having the amino acid sequence YTSSLHS (SEQ ID NO:7) and a CDR3 having the amino acid sequence QQYLAFPYTF (SEQ ID NO:8); and
b) an antibody VH domain comprising a CDR1 having the amino acid sequence GYTMN (SEQ ID NO:10), a CDR2 having the amino acid sequence LINPYNGGTSYNQN-FKG (SEQ ID NO:11) and a CDR3 having the amino acid sequence EDYDGYLYFAMDY (SEQ ID NO:12).

In a particular embodiment, the target binding member comprises a VL domain comprising SEQ ID NO:5 and a VH domain comprising SEQ ID NO:9. In a further embodiment, the target binding member comprises a whole antibody.

In various embodiments, the invention further relates to an isolated nucleic acid which comprises a nucleotide sequence encoding a target binding member of the invention, an expression vector comprising such nucleic acids and a host cell carrying such expression vectors.

In another embodiment, the invention relates to a method of producing a target binding member, the method comprising culturing a host cell of the invention under conditions for production of the target binding member.

In a further embodiment, the invention provides compositions comprising a target binding member of the invention and a pharmaceutically acceptable carrier.

In additional embodiments, the invention encompasses methods of treating or preventing a disease or condition in a subject in need thereof, including but not limited to asthma and inflammatory bowel disease.

In a further embodiment, the invention provides the use of target binding members of the invention, for example in the form of a pharmaceutical composition, for the treatment of diseases or conditions, including inflammatory conditions such as asthma (including allergic asthma), and inflammatory bowel disease (e.g., Crohn's disease and ulcerative colitis).

In another embodiment, the invention relates to a target binding member that competes for binding to IL-25 with a target binding member that binds one or more amino acid sequences selected from the group consisting of amino acid residues 46-63 of SEQ ID NO:17, amino acid residues 66-84 of SEQ ID NO:17 and amino acid residues 129-135 of SEQ ID NO:17. In a particular embodiment, the target binding member has a binding affinity for human IL-25 that is less than or equal to about 50 pM.

The invention further relates, in another embodiment, to a target binding member of the invention comprising:
a) an antibody VL domain comprising an amino acid sequence having from 1 to about 20 amino acid substitutions relative to the amino acid sequence of SEQ ID NO:5;
b) an antibody VH domain comprising an amino acid sequence having from 1 to about 20 amino acid substitutions relative to the amino acid sequence of SEQ ID NO:9; or
c) a combination thereof.

In yet another embodiment, the invention provides a method of producing a target binding member of the invention, comprising:
(a) providing a starting repertoire of nucleic acids encoding a VL domain wherein the nucleic acids either include a CDR3 encoding region to be replaced or lack a CDR3 encoding region;

(b) combining the starting repertoire with a donor nucleic acid encoding a VL CDR3 having the amino acid sequence QQYLAFPYTF (SEQ ID NO:8), wherein the donor nucleic acid is inserted into one or more nucleic acids in the repertoire to provide a product repertoire of nucleic acids encoding a VL domain comprising a VL CDR3 having the amino acid sequence QQYLAFPYTF (SEQ ID NO:8);

(c) expressing the nucleic acids of the product repertoire to provide target binding members;

(d) selecting a target binding member that specifically binds one or more sequences selected from the group consisting of amino acid residues 56-63 of SEQ ID NO:17, amino acid residues 66-74 of SEQ ID NO:17 and amino acid residues 129-135 of SEQ ID NO:17; and (e) recovering the target binding member or nucleic acid encoding the target binding member.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the kappa light chain nucleotide (SEQ ID NO:1) and amino acid (SEQ ID NO:2) sequence of the huDDG91/RH2.5_R71V antibody. Underlining in the amino acid sequence denotes the CDRs. Leader sequence is not included.

FIG. 2 shows the heavy chain nucleotide (SEQ ID NO:3) and amino acid (SEQ ID NO:4) sequence of the huDDG91/RH2.5_R71V antibody. Underlining in the amino acid sequence denotes the CDRs. Leader sequence is not included.

FIG. 3 is a table showing properties of 9 candidate monoclonal antibodies, including M6, which were identified by screening a 25-member combinatorial library based on the huDDG91/RH2.5_R71V antibody. Italics denotes numbers obtained from a different data set. R71V G1 refers to the huDDG91 antibody. The two R71V G1 rows represent measurements from two different data sets. huDDG91 LCDR1: amino acid residues 24-34 of SEQ ID NO: 2; huDDG91 LCDR3: amino acid residues 89-97 of SEQ ID NO: 2; huDDG91 HCDR3: amino acid residues 99-111 of SEQ ID NO: 4; I25M6 LCDR1: SEQ ID NO: 6; I25M6 LCDR3: SEQ ID NO: 8; I25M6 HCDR3: SEQ ID NO: 12; I25M10 LCDR1: SEQ ID NO: 6; I25M10 LCDR3: SEQ ID NO: 8; I25M10 HCDR3: SEQ ID NO: 24; I25M11 LCDR1: SEQ ID NO: 18; I25M11 LCDR3: SEQ ID NO: 21; I25M11 HCDR3: SEQ ID NO: 24; I25M20 LCDR1: SEQ ID NO: 6; I25M20 LCDR3: SEQ ID NO: 8; I25M20 HCDR3: SEQ ID NO: 25; I25M32 LCDR1: SEQ ID NO: 19; I25M32 LCDR3: SEQ ID NO: 22; I25M32 HCDR3: SEQ ID NO: 25; I25M28 LCDR1: SEQ ID NO: 6; I25M28 LCDR3: SEQ ID NO: 8; I25M28 HCDR3: SEQ ID NO: 26; I25M30 LCDR1: SEQ ID NO: 20; I25M30 LCDR3: SEQ ID NO: 23; I25M30 HCDR3: SEQ ID NO: 26; I25M31 LCDR1: SEQ ID NO: 6; I25M31 LCDR3: amino acid residues 89-97 of SEQ ID NO: 2; I25M31 HCDR3: SEQ ID NO: 26; I25M34 LCDR1: SEQ ID NO: 19; I25M34 LCDR3: SEQ ID NO: 22; I25M34 HCDR3: SEQ ID NO: 26.

FIG. 4A shows amino acid sequences of the light chain of the M6 antibody (SEQ ID NO:5) and its CDRs (SEQ ID NOS:6-8). Underlining in the amino acid sequence denotes the positions of the CDRs. Leader sequence is not included.

FIG. 4B shows amino acid sequences of the heavy chain of the M6 antibody (SEQ ID NO:9) and its CDRs (SEQ ID NOS:10-12). Underlining in the amino acid sequence denotes the positions of the CDRs. Leader sequence is not included.

FIGS. 6A and 6B are graphs showing enhanced suppression of IL-25 induced GROα production by M6 antibody relative to huDDG91 (M9) antibody in LS174T cells that were stimulated with recombinant human IL-25 for 24 hours. The graphs in FIGS. 6A and 6B represent data from two separate experiments.

FIG. 7A shows a sequence coverage map of amino acid residues 1-78 of human IL-25 (SEQ ID NO:13) with pepsin digestion with 2 M urea, 1 M TCEP, pH 3.0 quenching. Black line is a peptide observed.

FIG. 7B shows a sequence coverage map of amino acid residues 79-146 of human IL-25 (SEQ ID NO:14) with pepsin digestion with 2 M urea, 1 M TCEP, pH 3.0 quenching. Black line is a peptide observed.

FIGS. 8A and 8B show differences in deuteration levels for different segments of human IL-25 protein (SEQ ID NO: 15 and SEQ ID NO: 16) upon M6 antibody binding in H/D-exchange experiments. Each block represents a human IL-25 peptide and contains data for six time points, 150 s and 500 s at pH 6, as well as 150 s, 500 s, 1,500 s and 5,000 s at pH 7. Dark blue indicates no protection upon M6 antibody binding. Other colors indicate more deuteriums after on-solution/off-column exchange than after on-column/off-column exchange as shown in the right insert. A deuterium attached to either of the first two amino acid residues of each ion is lost during the analysis (digestion/separation/mass analysis in aqueous environment), accounting for the small gaps in the H/D-Ex pattern.

FIG. 10 shows the amino acid sequence of human IL-25 (SEQ ID NO:17).

DETAILED DESCRIPTION OF THE INVENTION

Figure 5:
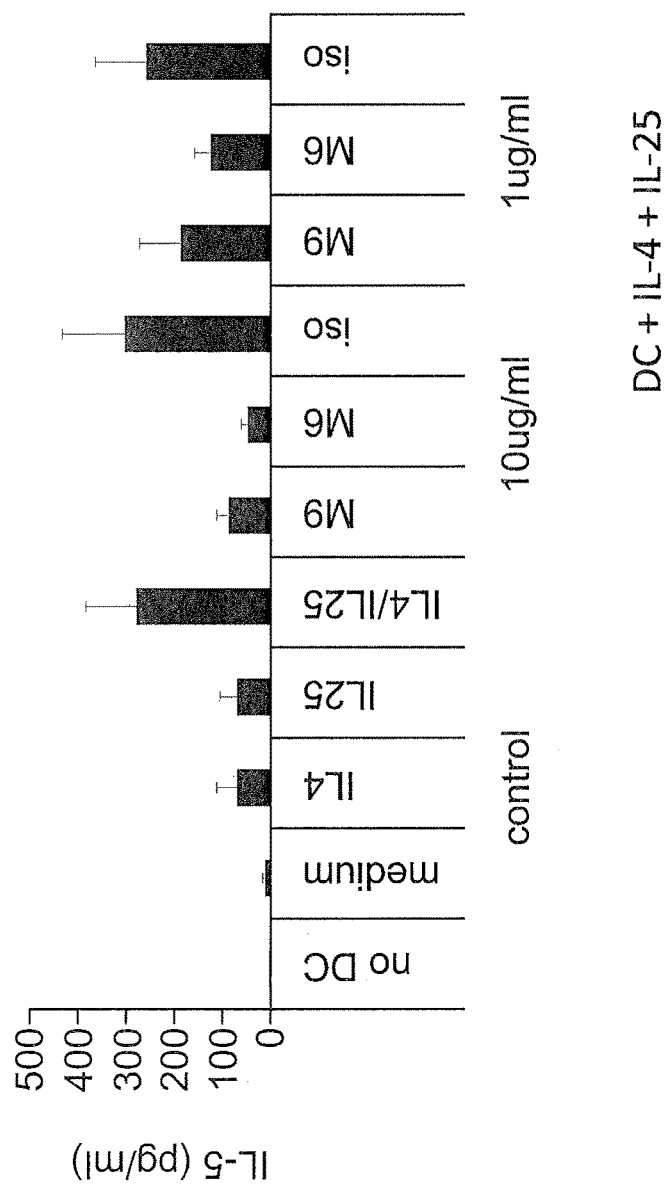
FIG. 5 is a graph showing that M6 suppresses IL-4/IL25-induced IL-5 production by naïve human CD4+ T cells that were stimulated for 4 days with autologous dendritic cells in the presence of rhIL-4 and rhIL-25 to a greater extent than huDDG91 (M9) antibody. An isotype IgG1 antibody (iso) served as a control. n=4 donors.

The present invention is based, in part, on the identification of a high affinity human IL-25 antibody, referred to herein as "M6" (see Example 1), and the identification of amino acid residues in human IL-25 that are bound by the M6 antibody, as determined by hydrogen/deuterium (H/D) exchange mass spectrometry (see Example 3). Accordingly, in one embodiment, the invention relates to a target binding member that binds IL-25, wherein the target binding member binds one or more amino acid sequences selected from the group consisting of amino acid residues 46-63, 66-84 and 129-135 of human IL-25 (SEQ ID NO:17). Thus, the target binding members of the invention can bind amino acid residues 46-63 of SEQ ID NO:17, amino acid residues 66-84 of SEQ ID NO:17, or amino acid residues 129-135 of SEQ ID NO:17, or any combination thereof. In one embodiment, the target binding members of the invention bind amino acids 56-63 of SEQ ID NO:17 and amino acids 66-74 of SEQ ID NO:17.

As used herein, "target binding member" refers to any protein or peptide containing molecule that comprises at least a portion of an immunoglobulin molecule that contains at least one complementarity determining region (CDR) of a heavy or light chain, or a ligand binding portion thereof, that specifically binds a mammalian (e.g., human) IL-25 protein, or a portion thereof. Such target binding members can further include at least a portion of an antibody heavy chain or light chain variable region, at least a portion of an antibody heavy chain or light chain constant region, at least a portion of an antibody framework region, or any combination thereof. Such target binding members modulate, decrease, antagonize, mitigate, alleviate, block, inhibit, abrogate and/or interfere with at least one IL-25 activity or binding, or with IL-25 receptor activity or binding, in vitro, in situ and/or in vivo. As a non-limiting example, a suitable target binding member of the present invention can bind with high affinity to an inhibiting and/or neutralizing epitope of human IL-25 recognized by the M6 antibody described herein.

The target binding members of the invention are not limited to those that bind only amino acid residues 46-63, amino acid residues 66-84, and/or amino acid residues 129-135 of SEQ ID NO:17. Thus, in some embodiments, the target binding members of the invention can additionally bind to one or more other portions of human IL-25 that do not encompass amino acid residues 46-63, amino acid residues 66-84, and/or amino acid residues 129-135 of SEQ ID NO:17. In other instances, target binding members of the invention can additionally bind to one or more amino acids residues in human IL-25 that flank amino acid residues 46-63, amino acid residues 66-84, and/or amino acid residues 129-135 of SEQ ID NO:17.

The invention further contemplates target binding members that bind one or more portions of human IL-25 that are encompassed within amino acid residues 46-63, amino acid residues 66-84, and/or amino acid residues 129-135 of SEQ ID NO:17, such as, for example, portions of IL-25 consisting of at least 5 amino acids of amino acid residues 46-63, amino acid residues 66-84, and/or amino acid residues 129-135 of SEQ ID NO:17. Exemplary portions of IL-25 that may be bound by target binding members include amino acids 56-63 and/or amino acids 66-74 of SEQ ID NO:17.

The region of IL-25, or epitope, bound by a target binding member of the invention can be determined using any of several standard epitope mapping techniques that are well known in the art to which the invention pertains. Such techniques include, for example, site-directed mutagenesis coupled with binding assays, epitope mapping with peptide pins (e.g., Geysen et al., *Peptides: Chemistry and Biological*, Proceedings of the Twelfth American Peptide Symposium, p. 519-523, Ed, G. R. Marshall, Escom, Leiden, 1988), X-ray crystallography, and hydrogen/deuterium (H/D) exchange techniques (e.g., H/D-exchange mass spectrometry).

As described herein, H/D-exchange mass spectrometry was employed to determine the epitope(s) in human IL-25 that is recognized and bound by the M6 antibody (see Example 3 and FIGS. 8A, 8B and 9A-9F). Upon transfer from water to a deuterium based solvent system (heavy water), a protein will experience an increase in mass as the protein's hydrogen atoms become gradually replaced with deuterons (heavier isotopes of hydrogen). The likelihood of a hydrogen/deuterium exchange event is largely determined by protein structure and solvent accessibility. H/D-exchange mass spectrometry is used to measure exchange and, as a consequence, protein structure and solvent accessibility. When a small molecule or protein binding partner binds to a protein target, that target experiences experimentally observable changes in its exchange rate. Surface regions that exclude solvent upon complex formation exchange much more slowly. Solvent-excluded regions are useful for deducing the location of a binding site. For instance, in the case of an antigen-antibody interaction, these changes highlight the location of the epitope.

Typically, a target binding member of the invention will comprise an antibody light chain variable region (VL) domain paired with an antibody heavy chain variable region (VH) domain to provide an IL-25 binding domain. In making the invention described herein, it was found that the binding affinity of the huDDG91 antibody was improved by altering a complementarity determining region (CDR) in the huDDG91 antibody VL domain (SEQ ID NO:2), specifically the CDR3 region, to QQYLAFPYTF (SEQ ID NO:8). Accordingly, the invention described herein contemplates VL domains comprising SEQ ID NO:8 and target binding members comprising such VL domains. In some embodiments, the VL domains in the target binding members of the invention also comprise the CDR1 (SASQGISNYLN (SEQ ID NO:6)) and CDR2 (YTSSLHS (SEQ ID NO:7)) regions from the M6 and huDDG91 antibodies. Other suitable VL CDR regions for inclusion in the target binding members of the invention include, but are not limited to, any of the VL CDR1 regions shown in FIG. 3. In one embodiment, target binding members of the invention comprise SEQ ID NO:5, the VL domain of the M6 antibody.

In some embodiments, target binding members of the invention also comprise a VH domain that comprises SEQ ID NOS:10-12, corresponding to the CDR regions of the M6 and huDDG91 antibodies. Other suitable VH CDR regions for inclusion in the target binding members of the invention include, but are not limited to, any of the VH CDR3 regions shown in FIG. 3. In a preferred embodiment, target binding members of the invention comprise SEQ ID NO:9, the VH domain of the M6 and huDDG91 antibodies. The VH domain may be paired with a number of VL domains other than the VL domain of the M6 antibody (SEQ ID NO:5). Preferably, the VH domain is paired with a VL domain comprising a CDR3 region comprising the amino acid sequence of SEQ ID NO:8.

The sequences of the CDRs of the M6 antibody described herein may be modified by insertions, substitutions and deletions and included in a target binding member of the invention to the extent that the target binding member (e.g., antibody) having the modified CDR(s) maintains the ability to bind to and inhibit human IL-25. The ordinarily skilled artisan can ascertain the maintenance of this activity by performing the functional assays described herein. A CDR in a target binding member of the invention can have, for example, from about 50% to about 100% homology, preferably from about 80% to about 100% homology, more preferably from about 90% to about 100% homology to a corresponding M6 CDR represented by SEQ ID NO:6, 7, 8, 10, 11 or 12. In one embodiment, a CDR in a target binding member of the invention can have about 100% homology to a corresponding M6 CDR represented by SEQ ID NO:6, 7, 8, 10, 11 or 12.

A target binding member according to the present invention may bind IL-25 with an affinity substantially similar to, or greater than, that of the M6 antibody described herein. For example, a target binding member of the invention can have a binding affinity for IL-25 (e.g., human IL-25) of about 50 pM (e.g., about 53 pM) or less, such as, for example about 45 pM, about 40 pM, about 35 pM, about 30 pM, about 25 pM or about 20 pM. A target binding member will generally be specific for IL-25. Thus, the target binding member will not show any significant binding to molecules other than its specific binding partner(s). For example, it has been found that the M6 antibody described herein does not cross-react with IL-17A, IL-17C, IL-17D or IL-17F. Avoidance of such crossreactivity to other cytokines implicated in asthma and similar processes is a desirable feature of target binding members in some embodiments of the invention.

The affinity or avidity of a target binding member an antigen can be determined experimentally using any suitable method. (See, for example, Berzofsky et al., "Antibody-Antigen Interactions," in *Fundamental Immunology*, Paul, W. E., Ed., Raven Press: New York, N.Y. (1984); Kuby, Janis, *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., KD, Ka, Kd) are preferably made with standardized solutions of antibody and antigen, and a standardized buffer, such as the buffer described herein.

For example, specificity may be determined by means of a binding assay such as an ELISA employing a panel of antigens, a Biacore assay and/or an Octet assay, among others. A target binding member according to the present invention may recognize IL-25 and not other members of the IL-17 family, particularly any one of IL-17A, IL-17B, IL-17C, IL-17D and IL-17F; in one embodiment, all five of these molecules. Binding of a target binding member according to the invention with IL-25 may be abolished by competition with recombinant IL-25.

Binding affinity and neutralization potency of different target binding members can be compared under appropriate conditions.

The invention also relates to a target binding member that competes for binding to IL-25 with a target binding member of the invention that binds one or more amino acid sequences selected from the group consisting of amino acid residues 46-63 of SEQ ID NO:17, amino acid residues 66-84 of SEQ ID NO:17 and amino acid residues 129-135 of SEQ ID NO:17). In a particular embodiment, the target binding member has a binding affinity for human IL-25 that is less than or equal to about 50 pM.

Competitive assays can be performed with the target binding member (e.g., antibody) of the present invention in order to determine what proteins, antibodies, and other antagonists compete for binding to IL-25 with the target binding member of the present invention and/or share the epitope region. These assays as readily known to those of ordinary skill in the art evaluate competition between antagonists or ligands for a limited number of binding sites on a protein, e.g., IL-25. The protein and/or antibody is immobilized or insolubilized before or after the competition and the sample bound to the IL-25 protein is separated from the unbound sample, for example, by decanting (where the protein/target binding member was preinsolubilized) or by centrifuging (where the protein/antibody was precipitated after the competitive reaction). Also, the competitive binding may be determined by whether function is altered by the binding or lack of binding of the target binding member to the protein, e.g., whether the target binding member molecule inhibits or potentiates the enzymatic activity of, for example, a label. ELISA and other functional assays may be used, as well known in the art.

Antibodies

Preferably, a target binding member of the invention is an antibody molecule. The term "antibody" is intended to encompass whole antibodies, digestion fragments, specified portions and variants thereof, including antibody mimetics or portions of antibodies that mimic the structure and/or function of an antibody or specified fragment or portion thereof, including single chain antibodies and fragments thereof; each containing at least one CDR. Functional fragments include antigen-binding fragments that bind to a mammalian IL-25. For example, antibody fragments capable of binding to IL-25 or portions thereof, including, but not limited to Fab (e.g., by papain digestion), Fab' (e.g., by pepsin digestion and partial reduction) and F(ab')$_2$ (e.g., by pepsin digestion), Facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, et al., eds., *Current Protocols in Immunology*, John Wiley & Sons, Inc., NY (1994 2001); Colligan et al., *Current Protocols in Protein Science*, John Wiley & Sons, NY, N.Y., (1997 2001)".

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

As used herein, the term "antibody" is also intended to encompass "chimeric" antibodies, and "humanized" or "CDR-grafted" antibodies that include any combination of the herein described M6 CDRs with one or more proteins or peptides derived from a non-murine, preferably, human antibody. In accordance with the invention, chimeric or humanized antibodies are provided wherein the CDRs are derived from the M6 antibody. Thus, in one embodiment, the human part of the antibody may include the regions which are substantially non-immunogenic in humans. The regions of the antibody that are derived from human antibodies need not have 100% identity with human antibodies. In a preferred embodiment, as many of the human amino acid residues as possible are retained in order for the immunogenicity to be negligible, but the human residues may be modified as necessary to support the antigen binding site formed by the CDRs while simultaneously maximizing the humanization of the antibody. Such changes or variations optionally and preferably retain or reduce the immunogenicity in humans or other species relative to non-modified antibodies. A humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Alternatively, the entire heavy chain variable region and light chain variable region of the M6 antibody in FIGS. 4A and 4B (SEQ ID NOS:5 and 9) may be combined with human constant and framework regions to form the target binding member of the present invention.

Human genes which encode the constant (C) regions of the target binding member of the present invention can be derived from a human fetal liver library, by known methods. Human C region genes can be derived from any human cell including those which express and produce human immunoglobulins. The human CH region can be derived from any of the known classes or isotypes of human H chains, including gamma, mu., alpha., delta., epsilon, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). In one embodiment, the CH region is derived from gamma 1 (IgG1).

The human CL region can be derived from either human L chain isotype, kappa or lambda, preferably kappa.

Genes encoding human immunoglobulin C regions can be obtained from human cells by standard cloning techniques (e.g., Sambrook et al. (*Molecular Cloning: A Laboratory Manual*, 2nd Edition, Cold Spring Harbor Press, Cold Spring Harbor, N.Y. (1989) and Ausubel et al., eds., *Current Protocols in Molecular Biology* (1987, 1993)). Human C region genes are readily available from known clones containing genes representing the two classes of L chains, the five classes of H chains and subclasses thereof. Chimeric antibody fragments, such as $F(ab_1)_2$ and Fab, can be prepared by designing a chimeric H chain gene which is appropriately truncated. For example, a chimeric gene encoding an H chain portion of an $F(ab_1)_2$ fragment would include DNA sequences encoding the CH1 domain and hinge region of the H chain, followed by a translational stop codon to yield the truncated molecule.

Generally, in one example, chimeric antibodies, fragments and regions of the present invention are produced by cloning DNA segments encoding the H and L chain antigen-binding regions of the M6 antibody, and joining these DNA segments to DNA segments encloding CH and CL regions, respectively, to produce chimeric immunoglobulin-encoding genes.

Thus, in one embodiment, a fused chimeric gene is created which comprises a first DNA segment that encodes at least an antigen-binding region of non-human origin, such as a functionally rearranged V region with joining (J) segment, linked to a second DNA segment encoding at least a part of a human C region.

The sequences of the variable regions of the M6 antibody may be modified by insertions, substitutions and deletions to the extent that the target binding member maintains the ability to bind to and inhibit human IL-25.

For convenience, the numbering scheme of Kabat et al., has been adopted herein. Residues are designated by lower case numbers or hyphens as necessary to conform the present sequences to the standard Kabat numbered sequence.

In accordance with the present invention, in the case of a CDR-grafted or humanized antibody where the CDR region of the M6 antibody is combined with a human region, residues may be retained in the FR region which are idiosyncratic to the parent antibody, e.g., M6. Residues that have been demonstrated to be critical in the humanization of other antibodies may also be retained. These guidelines can be followed to the extent necessary to support the antigen binding site formed by the CDRs while simultaneously maximizing the humanization of the antibody.

Methods for engineering or humanizing non-human or human antibodies can also be used and are well known in the art. Generally, a humanized or engineered antibody has one or more amino acid residues from a source which is non-human, e.g., but not limited to, mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., in a number of public databases such as the NCBI database of the National Institute of Health or publications such as Kabat et al., Sequences of Proteins of Immunological Interest, U.S. Dept. Health (1983).

Such imported sequences can be used to reduce immunogenicity or reduce, enhance or modify binding, affinity, on-rate, off-rate, avidity, specificity, half-life, or any other suitable characteristic, as known in the art. Generally, part or all of the non-human or human CDR sequences can be maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, (Jones et al., *Nature* 321:522 (1986); Riechmann et al., *Nature* 332:323 (1988); Verhoeyen et al., *Science* 239:1534 (1988)), Sims et al., *J. Immunol.* 151: 2296 (1993); Chothia and Lesk, *J. Mol. Biol.* 196:901 (1987), Carter et al., *Proc. Natl. Acad. Sci. U.S.A.* 89:4285 (1992); Presta et al., *J. Immunol.* 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, including the references cited therein.

The human constant region of a target binding member of the invention can be of any class (IgG, IgA, IgM, IgE, IgD, etc.) or isotype and can comprise a kappa or lambda light chain. In one embodiment, the human constant region comprises an IgG heavy chain or defined fragment, for example, at least one of isotypes, IgG1, IgG2, IgG3 or IgG4. In another embodiment, the target binding member comprises an IgG1 heavy chain and a IgG1 K light chain. The isolated target binding member of the present invention can comprise antibody amino acid sequences disclosed herein encoded by any suitable polynucleotide. Preferably, the target binding member binds human IL-25 and thereby partially or substantially neutralizes at least one biological activity of the protein. The target binding member, or specified portion or variant thereof, partially or preferably substantially neutralizes at least one biological activity of at least one IL-25 protein or fragment and thereby inhibits activities mediated through the binding of IL-25 to the IL-25 receptor or through other IL-25-dependent or mediated mechanisms. As used herein, the term "neutralizing antibody" refers to an antibody that can inhibit an IL-25-dependent activity by about 20-100%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of a target binding member to inhibit an IL-25-dependent activity is preferably assessed by at least one suitable IL-25 protein or receptor assay, as described herein and/or as known in the art.

At least one antibody of the invention binds at least one epitope specified herein to which the M6 antibody binds. The at least one epitope can comprise at least one antibody binding region that comprises at least one portion of the protein, which epitope is preferably comprised of at least one extracellular, soluble, hydrophillic, external or cytoplasmic portion of the protein. Generally, the target binding member of the present invention will comprise an antigen-binding region that comprises at least one complementarity determining region (CDR 1, CDR2 and CDR3) of SEQ ID NOS. 10, 11 and 12 or variant of at least one heavy chain variable region and at least one human complementarity determining region (CDR1, CDR2 and CDR3) (SEQ ID NO. 6, 7 and 8) or variant of at least one light chain variable region.

Target binding members that bind to human IL-25 and that comprise the defined heavy or light chain variable region or CDR regions can be prepared using suitable methods, such as phage display (Katsube, Y., et al., Int J. Mol. Med, 1(5):863 868 (1998)) or methods that employ transgenic animals, as known in the art and/or as described herein. For example, the antibody, specified portion or variant can be expressed using the encoding nucleic acid or portion thereof in a suitable host cell.

As stated, the invention also relates to antibodies, antigen-binding fragments, immunoglobulin chains and CDRs comprising amino acids in a sequence that is substantially the same as an M6 amino acid sequence described herein. Such anti-IL-25 antibodies can include one or more amino acid substitutions, deletions or additions, either from natural mutations or human manipulation, as specified herein. Preferably, such antibodies or antigen-binding fragments and antibodies comprising such chains or CDRs can bind human IL-25 with high affinity (e.g., KD less than or equal to about 10-9 M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

The number of amino acid substitutions a skilled artisan would make depends on many factors, including those described above. Generally speaking, the number of amino acid substitutions, insertions or deletions for any given anti-IL-25 antibody, fragment or variant will not be more than 40, 30, 20, 19, 18, 17, 16, 15, 14, 13, 12, 11, 10, 9, 8, 7, 6, 5, 4, 3, 2, or 1, such as 1-30 or any range or value therein, as specified herein.

Amino acids in a target binding member of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081 1085 (1989)). The latter procedure introduces single alanine mutations at every residue in the molecule. The resulting mutant molecules are then tested for biological activity, such as, but not limited to, at least one IL-25 neutralizing activity. Sites that are critical for antibody binding can also be identified by structural analysis such as crystallization, nuclear magnetic resonance or photoaffinity labeling (Smith, et al., J. Mol. Biol. 224:899 904 (1992) and de Vos, et al., Science 255:306 312 (1992)).

Target binding members of the present invention can include, but are not limited to, at least one portion, sequence or combination selected from 5 to all of the contiguous amino acids of at least one of SEQ ID NO:5-12.

A target binding member can further optionally comprise a polypeptide of at least one of 70-100% of the contiguous amino acids of at least one of SEQ ID NOS:5 or 9.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS:5 or 9. For example, the amino acid sequence of a light chain variable region can be compared with the sequence of SEQ ID NO:5, or the amino acid sequence of a heavy chain variable region can be compared with SEQ ID NO:9. Preferably, 70-100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS:5 and 9. The target binding members of the present invention, or specified variants thereof, can comprise any number of contiguous amino acid residues from an antibody of the present invention, wherein that number is selected from the group of integers consisting of from 10-100% of the number of contiguous residues in a target binding member. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50 %, 60%, or 70%, and most preferably at least 80%, 90%, or 95% or 100% of that of the native (non-synthetic), endogenous or related and known antibody. Methods of assaying and quantifying measures of enzymatic activity and substrate specificity are well known to those of skill in the art.

In another aspect, the invention relates to target binding members, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified target binding members of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-DELTA9-octadecanoate (C18, oleate), all cis-DELTA5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified target binding members can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group, thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see, for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified target binding members of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147 153 (1992); Werlen et al., *Bioconjugate Chem.*, 5:411 417 (1994); Kumaran et al., *Protein Sci.* 6(10):2233 2241 (1997); Itoh et al., *Bioorg. Chem.*, 24(1): 59 68 (1996); Capellas et al., *Biotechnol. Bioeng.*, 56(4):456 463 (1997)), and the methods described in Hermanson, G. T., *Bioconjugate Techniques*, Academic Press: San Diego, Calif. (1996).

Target binding members useful in the methods and compositions of the present invention are characterized by high affinity binding to IL-25 and optionally have low toxicity. In particular, a target binding member of the invention, where the individual components, such as the variable region, constant region and framework, individually and/or collectively, optionally and preferably possess low immunogenicity, is useful in the present invention. The target binding members that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titers in the patient treated (less than about 300, preferably less than about 100 measured with a double antigen enzyme immunoassay) Elliott et al., *Lancet* 344:1125 1127 (1994), entirely incorporated herein by reference).

Bispecific, heterospecific, heteroconjugate or similar antibodies can also be used that are monoclonal, humanized, antibodies that have binding specificities for at least two different antigens. In the present case, one of the binding specificities is for at least one IL-25 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature* 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., *EMBO J.* 10:3655 (1991), Suresh et al., *Methods in Enzymology* 121: 210 (1986), each entirely incorporated herein by reference.

IL-25

Il-25, also known in the art as IL-17E, is available from commercial sources (e.g. R&D Systems, MN, USA) or may be cloned or synthesized by reference to the sequences of IL-25 available in the art. The sequence of human IL-25 (SEQ ID NO:17) is shown in FIG. 10. For production of antibodies or use in immunoassays, any fragment or combination of fragments of an IL-25 protein (e.g., a recombinant IL-25 protein) may be used, particularly those truncated at the N-terminal. For example, commercially available recombinant human IL-25 (IL-17E) comprises the mature protein sequence of Tyr 33-Gly 177 of Accession No. Q9H293) and commercially available murine IL-25 comprises residues Val 17- Ala 169 of mouse IL-17E (Accession No. NP_542767).

Nucleic Acid Molecules

Using the information provided herein, a nucleic acid molecule of the present invention encoding at least one target binding member of the invention can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS:10-12) or light chain (e.g., SEQ ID NOS:6-8); nucleic acid molecules comprising the coding sequence for an anti-IL-25 variable region (e.g., SEQ ID NOS:5 or 9); and nucleic acid molecules which comprise a nucleotide sequence substantially different from those described above but which, due to the degeneracy of the genetic code, still encode at least one anti-IL-25 antibody as described herein and/or as known in the art. Of course, the genetic code is well known in the art. Thus, it would be routine for one skilled in the art to generate such degenerate nucleic acid variants that code for specific anti-IL-25 antibodies of the present invention. See, e.g., Ausubel, et al., supra, and such nucleic acid variants are included in the present invention.

As indicated herein, nucleic acid molecules of the present invention which comprise a nucleic acid encoding an anti-IL-25 antibody can include, but are not limited to, those encoding the amino acid sequence of an antibody fragment, by itself the coding sequence for the entire antibody or a portion thereof the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides which Selectively Hybridize to a Polynucleotide

The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70 to 100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein. Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, Supra; or Sambrook, Supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation shorter sequences.

Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors and Host Cells

The present invention also relates to vectors that include isolated nucleic acid molecules of the present invention, host cells that are genetically engineered with the recombinant vectors, and the production of at least one anti-IL-25 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1 4 and 16 18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29 17.42 and 18.1 18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (world wide web.atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenylation sequence from the bovine growth hormone gene. Sequences for accurate splicing of the transcript can also be included. An example of a splicing sequence is the VP1 intron from SV40 (Sprague, et al., J. Virol. 45:773 781 (1983)). Additionally, gene sequences to control replication in the host cell can be incorporated into the vector, as known in the art.

Compositions

The present invention also provides at least one target binding member composition comprising at least one, at least two, at least three, at least four, at least five, at least six or more target binding members, as described herein and/or as known in the art that are provided in a non-naturally occurring composition, mixture or form. Such composition percentages are by weight, volume, concentration, molarity, or molality as liquid or dry solutions, mixtures, suspension, emulsions or colloids, as known in the art or as described herein.

Compositions of the present invention can further comprise at least one of any suitable and effective amount of a composition or pharmaceutical composition comprising at least one anti-IL-25 target binding member to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella cytotoxin*, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and *Streptococci*. See, e.g., Stein, ed., INTERNAL MEDICINE, 3rd ed., pp 1 13, Little, Brown and Co., Boston, (1990); Evans et al., eds., Bacterial Infections of Humans: Epidemiology and Control, 2d. Ed., pp 239 254, Plenum Medical Book Co., New York (1991); Mandell et al, Principles and Practice of Infectious Diseases, 3d. Ed., Churchill Livingstone, N.Y. (1990); Berkow et al, eds., The Merck Manual, 16th edition, Merck and Co., Rahway, N.J., 1992; Wood et al, FEMS Microbiology Immunology, 76:121 134 (1991); Marrack et al, Science, 248:705 711 (1990), the contents of which references are incorporated entirely herein by reference.

The compositions of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990. Pharmaceutically acceptable carriers can be routinely selected that are suitable for the mode of administration, solubility and/or stability of the anti-IL-25 target binding member, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1 99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

The compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, compositions of the invention can include polymeric excipients/additives such as polyvinylpyrrolidones, ficolls (a polymeric sugar), dextrates (e.g., cyclodextrins, such as 2-hydroxypropyl-.beta.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the compositions according to the invention are known in the art, e.g., as listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Therapeutic Applications

The present invention, in one aspect, provides a method of preventing or reducing airway hyperresponsiveness in a subject (e.g. a human) in need of treatment which comprises administering to the subject a target binding member, particularly an antibody molecule, that binds IL-25. In another aspect the invention provides a method of preventing, reducing or treating asthma in a subject in need of treatment which comprises administering to the subject a target binding member, particularly an antibody molecule, that binds IL-25. Asthma includes allergic asthma.

The above methods may be practiced with target binding members (including compositions thereof) according to the present invention, which are useful in binding to and preferably antagonizing action of IL 25, with therapeutic potential in various diseases and disorders in which IL-25 plays a role. In addition to asthma, such diseases include other conditions associated with inflammation, such as Inflammatory Bowel Disease (IBD), e.g., Crohn's disease and ulcerative colitis. The methods may also be practiced with other target binding members (including compositions thereof) which bind IL-25 that may be obtained as described below in the accompanying examples.

Target binding members (including compositions thereof) according to the invention may be used in a method of treatment (including prophylactic treatment) or diagnosis in human or animal subject. Such a method of treatment or diagnosis (which may include prophylactic treatment) may comprise administering to said subject an effective amount of a target binding member of the invention. Exemplary diseases and disorders are discussed further below.

Also provided is the use of a target binding member (including a compositions thereof) of the invention in the manufacture of a medicament for administration, to a human or animal subject.

Clinical indications in which an anti-IL-25 target binding member may be used to provide therapeutic benefit include any condition in which IL-25 has pathological consequences. Thus, in general, the target binding member of the invention may be used in the treatment of any condition associated with an unwanted Th2 response or type-2 responses. For example, the target binding member of the invention may be used for the treatment of allergy and asthma, particularly asthma.

Anti-IL-25 treatment may be given by injection (e.g. intravenously) or by local delivery methods. Anti-IL-25 may be delivered by gene-mediated technologies. Alternative formulation strategies may provide preparations suitable for oral or suppository route. The route of administration may be determined by the physicochemical characteristics of the treatment, by special considerations for the disease, to optimize efficacy or to minimize side-effects.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 0.5 mg-1.0 g, and this may be administered intravenously as a bolus or as an infusion over several hours as appropriate to achieve the required dose. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

A further mode of administration employs precoating of, or otherwise incorporation into, indwelling devices, for which the optimal amount of antibody will be determined by means of appropriate experiments.

An antibody molecule in some preferred embodiments of the invention is a monomeric fragment, such as F(ab) or scFv. Such antibody fragments may have the advantage of a relatively short half life and less risk of platelet activation, which may be caused by receptor clustering. Clustering which gives rise to platelet activation could be either of IL-25 molecules or of IL-25 with FcγRII molecules, for instance.

If a whole antibody is used, it is preferably in a form that is unable to activate and/or destroy platelets. The IgG4 isotype or alternatively "designer" isotypes derived from the IgG1 backbone (novel Fc gene constructs WO99/58572, Clark, Armour, Williamson) are preferred choices. Smaller antibody fragments may be used, such as F(ab')2. In addition, whole antibodies or fragments (e.g. F(ab')2 or diabodies) with dual epitope specificity (e.g. for the epitopes recognized by scFv 2C3) may be used. Although such an embodiment may promote receptor clustering, a high association rate to individual receptors may rule out this problem.

Target binding members of the present invention will usually be administered in the form of a pharmaceutical composition, which may comprise at least one component in addition to the target binding member.

A target binding member of the invention may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine; the administration of anti-emetics; or the administration of at least one other compound active against asthma, generally a bronchodilating agent which produces airway relaxation or enhances mucus clearance, e.g. a beta-agonist (e.g. salbutamol, salmeterol), disodium cromoglycate, steroids or an inhibitor of PDEIV.

Assay Methods

The present invention provides a method comprising causing or allowing binding of a target binding member as provided herein to IL-25. As noted, such binding may take place in vivo, e.g., following administration of a target binding member, or nucleic acid encoding a target binding member, or it may take place in vitro, for example in ELISA, Biacore assay, Octet assay, Western blotting, immuno-cytochemistry, immunoprecipitation or affinity chromatography.

The amount of binding of target binding member to IL-25 may be determined. Quantitation may be related to the amount of the antigen in a test sample, which may be of diagnostic interest.

The reactivities of antibodies on a sample may be determined by any appropriate means. Radioimmunoassay (RIA) is one possibility. Radioactive labeled antigen is mixed with unlabeled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a target binding member as above for measuring antigen levels in a competition assay, that is to say a method of measuring the level of antigen in a sample by employing a target binding member as provided by the present invention in a competition assay. This may be where the physical separation of bound from unbound antigen is not required. Linking a reporter molecule to the target binding member so that a physical or optical change occurs on binding is one possibility. The reporter molecule may directly or indirectly generate detectable, and preferably measurable, signals. The linkage of reporter molecules may be directly or indirectly, covalently, e.g., via a peptide bond or non-covalently. Linkage via a peptide bond may be as a result of recombinant expression of a gene fusion encoding antibody and reporter molecule.

The present invention also provides for measuring levels of antigen directly, by employing a target binding member according to the invention for example in a biosensor system.

Those skilled in the art are able to choose a suitable mode or binding according to their preference and general knowledge.

EXAMPLES

A description of example embodiments of the invention follows.

Example 1

Generation of M6, a High Affinity Humanized IL-25 Antibody huDDG91, a humanized (CDR-grafted) version of the murine 2C3 monoclonal anti-IL25 antibody, was chosen as a parent molecule for the generation of variants having improved binding affinity for IL-25. The kappa light chain sequence of huDDG91, excluding its leader sequence, is shown in FIG. 1 (SEQ ID NO:2), wherein the amino acid sequences of the CDR loops, as defined by Kabat, are underlined. The sequence of the huDDG91 heavy chain (SEQ ID NO:4) is shown in FIG. 2, wherein the amino acid sequence of the CDRs, as defined by Kabat, are underlined. huDDG91 is also known as RH2.5_R71V. The generation and characterization of murine 2C3 monoclonal anti-IL25 antibody is described in International Application No.: PCT/GB2008/001365, published on 30 Oct. 2008 as WO2008/129263, the contents of which are incorporated herein by reference in their entirety.

To generate variants of huDDG91, phage display libraries based on the huDDG91 sequence were constructed using standard methodology. The Fab libraries were panned against biotinylated IL-25. Fabs showing binding comparable or better than huDDG91 (IgG4) by ELISA were selected.

The Fabs were converted to mAbs as follows. A combinatorial library of 5 different light chains and 5 different heavy chains (including the huDDG91 light and heavy chains) was designed. The light and heavy chains used in the library differed from one another in the light chain CDR1 and CDR3 amino acid sequences and the heavy chain CDR 3 sequence. Using these light and heavy chains, a total of 25 mAbs (IgG1) were constructed, expressed in HEK293 cells at small scale and purified. Each of the mAbs was tested for IL-25 binding affinity, cellular inhibition, and receptor inhibition as follows:

IL-25 binding affinity was determined using standard IL-25 ELISA and Biacore binding assays. Candidates having a $K_D$ of less than 50 pM for human IL-25 and a $K_D$ of greater than 100 nM for human IL-17A, C, D and F were selected;

Cellular inhibition was assessed using a standard TK-10 human renal carcinoma cell-based assay (IL-25 responsive; IL-25 and IL-8 readout; capable of discerning difference between soluble IL-25R and parental mAb) and a CD4+ T cell-based assay. For the TK-10 assay, mAbs displaying an IC50 that was lower than parental huDDG91 antibody and >90% inhibition of IL-25 release at 10 nM mAb concentration were selected. For the CD4+ T cell assay, mAbs causing an inhibition of IL-5 production that was greater than or equal to that exhibited by parental huDDG91 were selected;

Receptor inhibition was assessed using a modified bead-based electrochemiluminescence immunoassay (ECLIA). Candidates causing a greater than 3-fold decrease in IC50 of IL-25 binding to receptor relative to parental huDDG91 antibody at a 10 nM mAb concentration were selected.

Based on these criteria, 9 candidate mAbs were selected (FIG. 3). All candidates showed acceptable expression levels and displayed desirable SE-HPLC and SDS-PAGE profiles when expressed in HEK293 and purified using standard protocols. These 9 candidates were then expressed transiently at 10 L scale in Chinese hamster ovary (CHO) cells, purified using Mab Select SuRe (GE Healthcare Life Sciences), buffer exchanged into phosphate buffered saline (PBS) and concentrated. The IL-25 binding affinity for each of the 9 candidate mAbs was significantly improved compared to huDDG91. Each of the mAbs was also tested for expression level, identity (SDS-PAGE), solubility, aggregation (SE-HPLC), post-translational modifications, protein-protein interactions and oxidation using routine techniques and assays. Several of the candidate mAbs displayed precipitation during concentration, low yields and/or undesirable SDS-PAGE and SE-HPLC profiles when expressed in CHO, purified, and processed under standard conditions.

One mAb, designated M6, was selected for further studies based on superior expression level, high solubility, lack of significant protein aggregation upon purification, and absence of undesired post-translational modifications, protein-protein interactions and oxidation upon purification.

Example 2

Characterization of the M6 Antibody

Materials and Methods

LS174T Human Colonic Epithelial Cell Assay

The human colonic epithelial cell line LS 174T (CL-188) was obtained from ATCC (Manassas, VA) and maintained in Dulbecco's modified eagle's medium (DMEM) (Invitrogen, Carlsbad, CA) supplemented with 10% FBS, penicillin and streptomycin at 37° C. under 5% $CO_2$. Cells were seeded in a 96-well tissue culture plate at a density of 1×105 cells/ml in a total volume of 100 μl and allowed to attach overnight. IL-25 antibodies (M6 and M9) were pre-complexed with recombinant human IL-25 protein (Centocor) with a constant amount of IL-25 protein (10 ng/ml final concentration) mixed with varying amounts of anti-IL-25 antibody titrated in a three-fold dilution or half-log dilution series and incubated at 37° C. for 1 hr. Cell culture medium was gently aspirated and replaced with the IL-25 protein /IL-25 antibody complex and cells were then incubated overnight for 18-18 hr. Culture plates were then centrifuged at 1200 rpm for 2 minutes to eliminate carryover of cellular debris and supernatant was then collected and assayed for GROα using an ELISA format (R&D Systems, Minneapolis, MN).

Results

Sequence analysis of M6 revealed a total of three amino acid substitutions relative to the huDDG91 sequence, all of which were present in the CDR3 of the light chain (see FIG. 3). The amino acid sequences of the light (SEQ ID NO:5) and heavy (SEQ ID NO:9) chains of M6 and their CDRs are shown in FIG. 4.

M6 was determined by Biacore to have a binding affinity for human IL-25 that is 3-5 fold higher than the affinity of huDDG91 for human IL25 (FIG. 3). Moreover, M6 was selective for IL-25, as it did not bind human IL-17A, C, D or F. Species cross-reactivity of M6 was assessed on cynomolgus monkey 12-25 cynoIL-25 and rodent (mouse) IL-25. Species cross-reactivity with cynoIL-25 was indicated by an affinity within 5 fold of human IL-25, inhibition in receptor ligand and TK-10 cell based assays. Using these criteria, it was determined that M6 bound to both cyno- and mouse IL-25.

Using the cell-based assays described in Example 1, M6 was shown to exhibit increased receptor inhibition relative to huDDG91, displaying a more than 3-fold decrease in IC50 compared to huDDG91 (FIG. 3). In addition, using the cell-based assays described in Example 1, M6 displayed increased cellular inhibition of human IL25 compared to huDDG91 (FIGS. 3 and 5). This result was confirmed by an LS 174T human colonic epithelial cell assay (FIGS. 6A and 6B), performed as described above.

Example 3

H/D-Exchange Mapping of the Epitope in Human IL-25 Recognized by M6

Summary

The putative epitope in human IL-25 recognized by the M6 antibody was mapped using ExSar™ hydrogen/deuterium exchange mass spectrometry performed by ExSar Corporation (Monmouth Junction, N.J.).

Materials and Methods

I. Digestion/Separation Optimization of IL-25

(1) Thawed IL-25 on ice (2) Split into 18×100 μL aliquots and froze them except one (3) Mixed 10 μL, of 0.28 mg/mL (16.6 μM) of IL-25 with 30 μL of PBS, pH 7.0 in water→[IL-25]=0.07 mg/mL (4.2 μM)

(4) Mixed 40 μL of (3) with various quenching solutions (5) Injected 55 μL into the ExSAR system (6) Passed sample over an immobilized pepsin column at 200 μL/min in buffer A (0.05% TFA in H2O)

(7) Peptic fragments were loaded onto a reversed-phase trap column and desalted with buffer A at 200 μL/min for 3 min (8) Peptic peptides were separated by a C18 column with a linear gradient of 13%→40% Buffer B (95% acetonitrile, 5% H2O, 0.0025% TFA) in 23 min (9) Peptides were detected by mass spectrometry II. Immobilization of M6

4.1. Experimental Procedure for Immobilization of M6

<Conjugation of Antibody on the Resin>

(1) Thawed 1.5 mL of 0.96 mg/mL M6 on ice (2) Used 400 μL (refroze unused material)

(3) Added 4 mg $NaCNBH_3$ (87.5 mmol) to a 1.5 mL screw top vial→40 mg of $NaCNBH_3$ per 1 g of POROS AL (4) Added 400 μL of the antibody solution to the vial (5) Made sure $NaCNBH_3$ dissolved before adding POROS AL resin (6) Placed 100 mg of POROS AL in the vial (7) Incubated the coupling reaction at room temperature with shaking for 3 h (8) Added a total volume of 400 μL of 2.8 M $Na_2SO_4$ in 5×80 μL portions, one portion per hour→[antibody]=0.48 mg/mL, [$NaCNBH_3$]=5.0 mg/mL [$Na_2SO_4$]=1.4 M.

(9) The mixture was shaken at room temperature overnight

(10) Washed the mixture with copious amount of PBS buffer, pH 7.0 using a filter funnel <Capping>

(11) Prepared capping solution by mixing 250 μL of ethanolamine (FW=61.08, density=1.012 g/mL, 8.3 mmol, ~1 M) to 3.5 mL PBS, pH 7.0 and adjusting the pH of this solution to pH 7.2 with glacial acetic acid (~200 μL). A final volume of the solution is close to 4 ml.

(12) 4 mg of NaCNBH3 was dissolved in 500 µL of the capping solution→[NaCNBH$_3$]=8 mg/mL, [ethanolamine]=~1 M.
(13) Resuspended the washed dried resin in the NaCNBH$_3$ solution
(14) Shook for 2 h at room temperature
(15) The mixture was filtered and washed with copious amount of PBS, pH 7.0 using a filter funnel.
(16) Re-suspended the resin cake in 0.75 mL PBS buffer, pH 7.0.
(17) Stored the conjugated material in refrigerator at 4° C.

III. Experimental Procedure for Binding Capacity Test of M6 Column

<Preparation of Buffers>
(1) Prepared 50 mM citrate, pH 6.0 in water
(2) Prepared 50 mM citrate, 2 mM Foscholine-12, pH 6.0 in water
(3) Prepared PBS, pH 7.0 in water
(4) Either (1), (2) or (3) was used as "buffer H"

<Binding Capacity Test>
(5) An mAb column (104 µL) was packed with 600 µL of M6 coupled to POROS resin using a 500 µL/min flow of buffer A (0.05% TFA in H$_2$O) and a 2.1 mm×30 mm stainless steel column holder
(6) The antibody column was placed in the reservoir bath of a chiller unit set to 3° C. with lines set for delivery and capture of reagent in and out of the column. A 2 micrometer frit was placed in line with the input line for filtering reagents and samples.
(7) The antibody column was equilibrated with 2×250 µL of "buffer H". Used a pH paper to test the pH of the solution at the end of the line to make sure the pH is neutral.
(8) Mixed 10 µL of 0.28 mg/mL (16.6 µM) of IL-25 with 30 µL of "buffer H"→[IL-25]=4.1 µM (equivalent to 166 pmol)
(9) Injected the above mixture onto the equilibrated antibody column.
(10) 200 µL of "buffer H" (placed in a 500 µL Hamilton syringe) was delivered to the column at 3° C. using a syringe pump and 5×40 µL fractions are collected.
(11) 200 µL of 0.8% formic acid was delivered to the column using a syringe pump at 3° C. and 5×40 µL fractions were collected.
(12) A control injection was prepared in a glass insert by mixing 10 µL of 0.28 mg/mL (16.6 µM) of IL-25 with 30 µL of "buffer H"
(13) Centrifuged all inserts containing the fractions or the control sample to spin down all liquid on the wall of the insert. Capped and labeled vials with inserts inside.
(14) Kept neutral and acid fractions as well as the control sample in cool stack tray 4 from 3 to 23 in odd positions following the order of control sample, neutral wash 1, 2, 3, 4, 5 and acid wash 1, 2, 3, 4, 5.
(15) Eleven capped empty vials were positioned at cool stack tray 4 from 4 to 24 in even positions.
(16) Mixed each fraction with 20 µL of 2 M urea, 1 M TCEP, pH 3.0.
(17) Injected 55 µL of the quenched solution into ExSAR's system without pepsin columns.
(18) The sample was loaded onto a trap column at 200 µL/min in buffer A (0.05% TFA), desalted for 3 min, and eluted with a linear gradient of 13% to 40% buffer B (95% acetonitrile, 5% H2O, 0.0025% TFA) over 23 min.
(19) Eluates were analyzed by mass spectrometry in MS1: Centroid mode.

IV. Experimental Procedure for On-Solution/Off-Column Exchange

<Preparation of Buffers>
(1) Prepared 50 mM citrate, 2 mM Foscholine-12, pH 6.0 in H$_2$O
(2) Prepared PBS, 2 mM Foscholine-12, pH 7.0 in H$_2$O
(3) Prepared PBS, pH 7.0 in H$_2$O
(4) Used (1)-(3) as "exchange H"
(5) Prepared "exchange HH" by mixing 1 parts of PBS, pH 7.0 in H$_2$O and 3 part of "exchange H"
(6) Prepared 50 mM citrate, 2 mM Foscholine-12, pH 6.0 in D$_2$O
(7) Prepared PBS, 2 mM Foscholine-12, pH 7.0 in D$_2$O
(8) Prepared PBS, pH 7.0 in D$_2$O
(9) Used (6)-(8) as "exchange D"
(10) Prepared "exchange HD" by mixing 1 parts of PBS, pH 7.0 in H$_2$O and 3 part of "exchange D"

<On-Solution>
(1) Positioned and equilibrated the mAb column (104 µL bed volume) inside a cool box at 3° C.
(2) Cleaned the mAb column with 2×250 µL of 0.8% formic acid
(3) Washed the mAb column with 2×250 µL of "exchange HD" to equilibrate the column
(4) Mixed 10 µL of 0.28 mg/mL (16.6 µM) of IL-25 with 30 µL of "exchange D" at 3° C.→>[IL-25]=0.07 mg/mL (4.2 µM), [D20]=75% (Start timer for on-exchange)
(5) Incubated the mixture for 150, 500, 1,500 or 5,000 s at 3° C.
(6) Injected the mixture (40 µL) onto the mAb column
(7) Washed the mAb column with 100 µL of "exchange HD" at 3° C.

<Off-Column>
(8) Washed the mAb column with 200 µL of a chilled "exchange HH" (stop on-exchange time and start off-exchange time as soon as H$_2$O touches the column)
(9) Incubated at 23° C. for 75 250, 750 or 2,500 s <Elution>
(10) Injected 120 µL of a chilled 0.8% formic acid onto the mAb column (stop off-exchange time as soon as acid is introduced to the column)
(11) Injected an additional 40 µL of a chilled 0.8% formic acid to elute antigen from the mAb column
(12) Collected this 40 µL fraction using a glass insert <Analysis>
(13) Added 20 µL of a chilled 2 M urea, 1 M TCEP, pH 3.0 into 40 µL fraction
(14) Injected 55 µL of quenched exchanged sample into the ExSAR system with pepsin column and C18 column (pepsin column 104 µL bed volume; flow rate over pepsin column 200 µL/min; C18 gradient 13%-40% buffer B over 23 min). Set digestion time as 3 min.
(15) The eluates were analyze by mass spectrometer in MS1: Profile V. Experimental Procedure for On-Column/Off-Column Exchange <On-Column>
(1) Positioned and equilibrated the mAb column (104 µL bed volume) inside a cool box at 23° C.
(2) Cleaned the mAb column with 2×250 µL of 0.8% formic acid
(3) Washed the mAb column with "exchange HH" to equilibrate the column (4) Mixed 10 µL of 0.28 mg/mL (16.6 µM) of IL-25 with 30 µL of "exchange H" at 3° C.→[IL-25]=0.07 mg/mL (4.2 µM), [D₂O]=0%
(5) Injected the mixture on the mAb column
(6) Washed with 100 µL of "exchange HH"
(7) The on-exchange reaction was initiated by passing 200 µL of "exchange HD" over the mAb column (Start on-exchange time)
(8) Incubated the mAb column for 150, 500, 1,500 or 5,000 s at 3° C.
<Off-Column> The same as 5.2
<Elution> Same as procedure IV, steps 10-14 above.
<Analysis> Same as procedure IV, step 15 above.
VI. Experimental Procedure for Fully Deuterated Experiment
<Preparation of Fully Deuterated Sample>
(1) Mixed 10 µL of 0.28 mg/mL (16.6 µM) of IL-25 with 30 µL of "exchange D",
(2) Heated the mixture at 60° C. for 3 h
(3) Cooled it to room temp
(4) Loaded the 40 µL mixture to the mAb column
(5) Injected 100 µL of "exchange HD" into the mAb column
<Elution> Same as procedure IV, steps 10-14 above.
<Analysis> Same as procedure IV, step 15 above.

Any deuterium attached on the first two amino acid residues of each ion was lost during the analysis (digestion/separation/mass analysis in aqueous environment). This accounts for the small gaps in the H/D-Ex pattern in FIGS. 8A and 8B. Non-deuterated experiments, on-exchange experiments, and fully deuterated experiments were run for each protein. The non-deuterated experiments were for identification of ions as well as the precise m/z of each ion without deuterium. The fully deuterated experiments identified the deuterium loss for each ion during the analysis (digestion/separation/mass analysis in aqueous environment). In these types of experiments, the number of deuterons prior to LCMS analysis and following the on or on-off exchange reaction can be back calculated. For on-off exchange experiments, the off-exchange time was a half of the on-exchange time. This is due to the fact that the intrinsic H→D exchange rate is a half of the intrinsic D→H exchange rate for the same pH reading.

Results

IL-25 Digestion

IL-25 was digested by pepsin with various conditions. The best digestion of IL-25 with pepsin was obtained when 2 parts of diluted IL-25 solution was quenched with 1 part of 2 M urea, 1 M TCEP, pH 3.0 and digested by a pepsin column at 200 µL/min. The best separation condition was a C18 column with a linear gradient of 13% to 40% buffer B (95% acetonitrile, 5% H2O, and 0.0025% TFA) in buffer A for 23 min. The sequence coverage of IL-25 after pepsin digestion was 100% (=146/146; FIGS. 7A and 7B).

Immobilization of M6 and Binding Capacity Test of M6 Column

The IL-25 sample without pepsin digestion showed one chromatographic peak at 8.5 min. The sample appeared clean. M6 was successfully conjugated on POROS AL resin by Schiff's base chemistry. ExSAR tested the binding capacity of a M6 column in three different conditions as shown in Table 1. An intact peak with m/z=1875 (+18) and 1985 (+17) were followed. In all binding conditions tested, no IL-25 was eluted out in neutral washing, indicating that all IL-25 loaded (166 pmol) binds to the M6 column at neutral conditions. IL-25 may stick to the M6 column non-specifically. Only 17-18% of IL-25 loaded was recovered in acid washing in the absence of detergent. Also the back pressure of M6 column gradually increased as IL-25 was loaded repeatedly. The recovery improved by the addition of Foscholine-12.

TABLE 1

Conditions employed for testing binding capacity of M6 antibody column

| "buffer H" | temperature | pepsin | neutral | acid |
|---|---|---|---|---|
| (a) 50 mM citrate, pH 6 | 3° C. | — | 0% | 18% |
| (b) 50 mM citrate, 2 mM Foscholine-12, pH 6 | 3° C. | — | 0% | 24% |
| (c) PBS, pH 7 | 3° C. | — | 0% | 17% |

The column between "temperature" and "neutral" is entitled "pepsin".

Epitope Identification

<On-Exchange Experiments of IL-25 in Solution>

On-exchange experiments of IL-25 in solution were carried out at 23° C. at pH 7. IL-25 was shown to be a relatively dynamic protein.

<On/Off-Exchange Experiments of IL-25 with or without M6 Column>

Figure 8B:
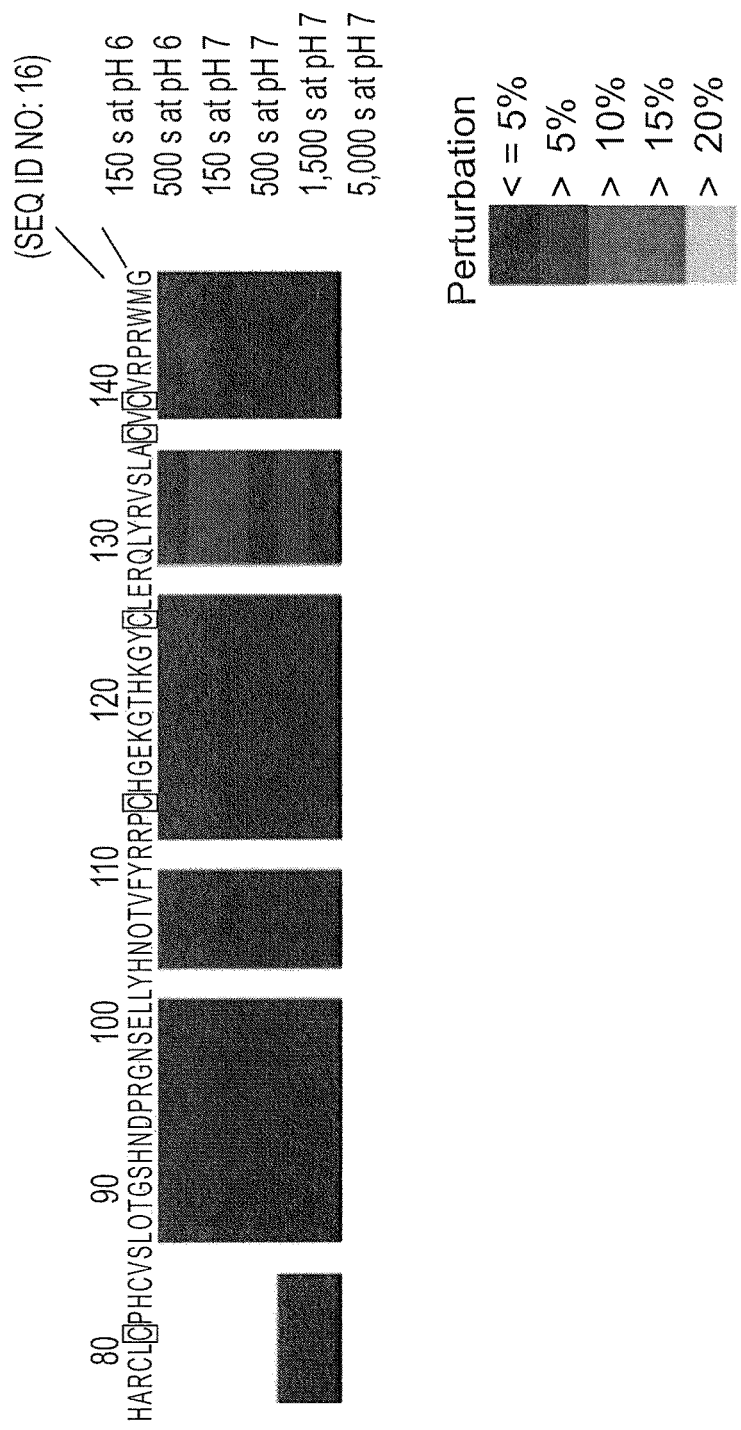
Figure 9A:
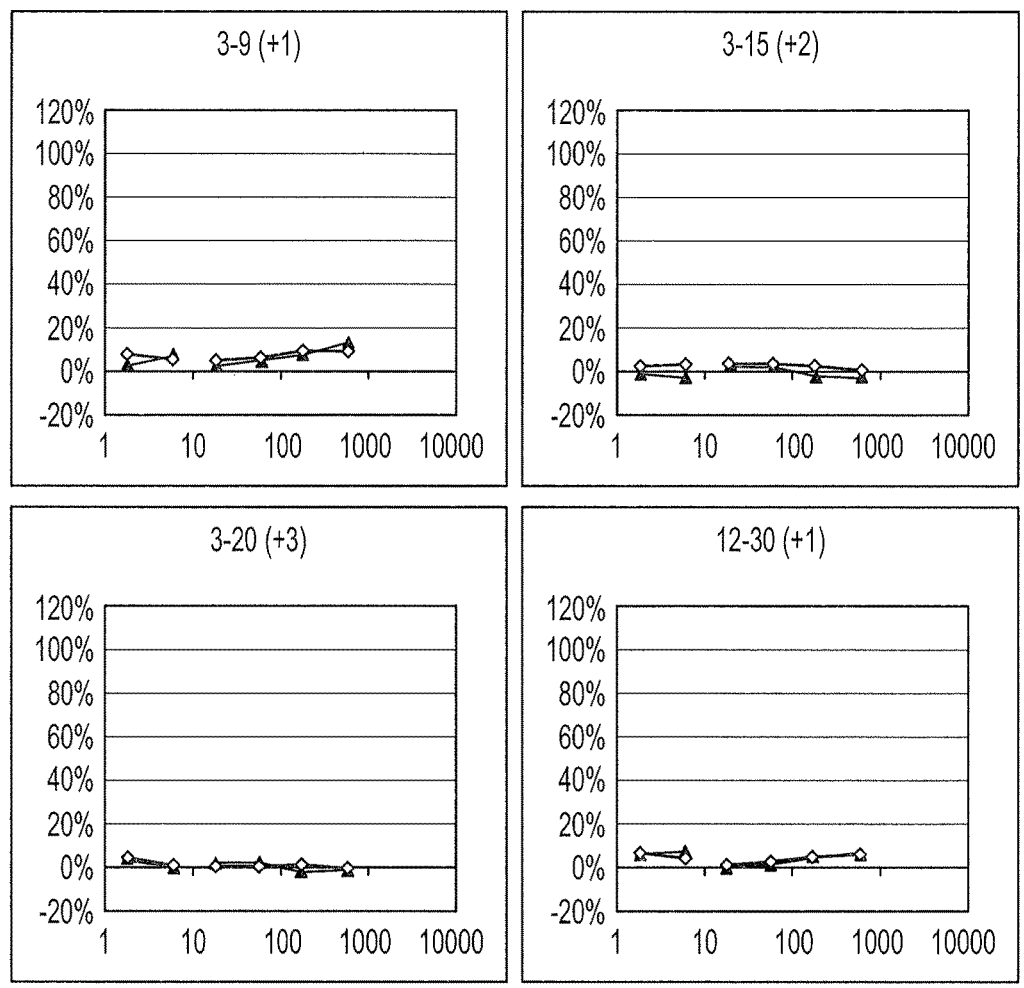
FIGS. 9A-9F are graphs showing deuterium content in different segments of human IL-25 after on/off exchange at pH 6 and pH 7 at 3° C. with an M6 antibody column. Blue, on-solution/off-column and purple, on-column/off-column. All exchange times are converted into pH 7 at 23° C. equivalent (e.g., 150 s at pH 6 at 3° C. is equal to 1.85 s at pH 7 at 23° C.). Human IL-25 residues represented in each segment are indicated at the top of each plot.
Figure 9B:
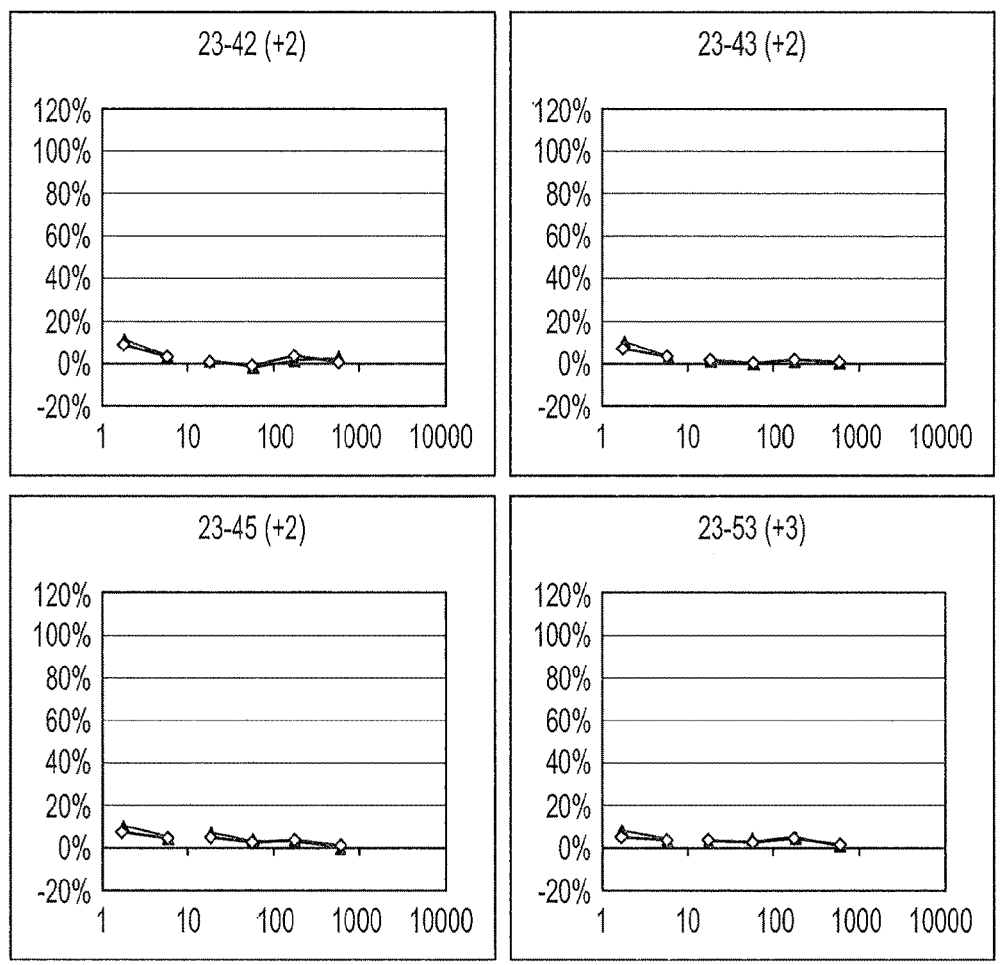
Figure 9C:
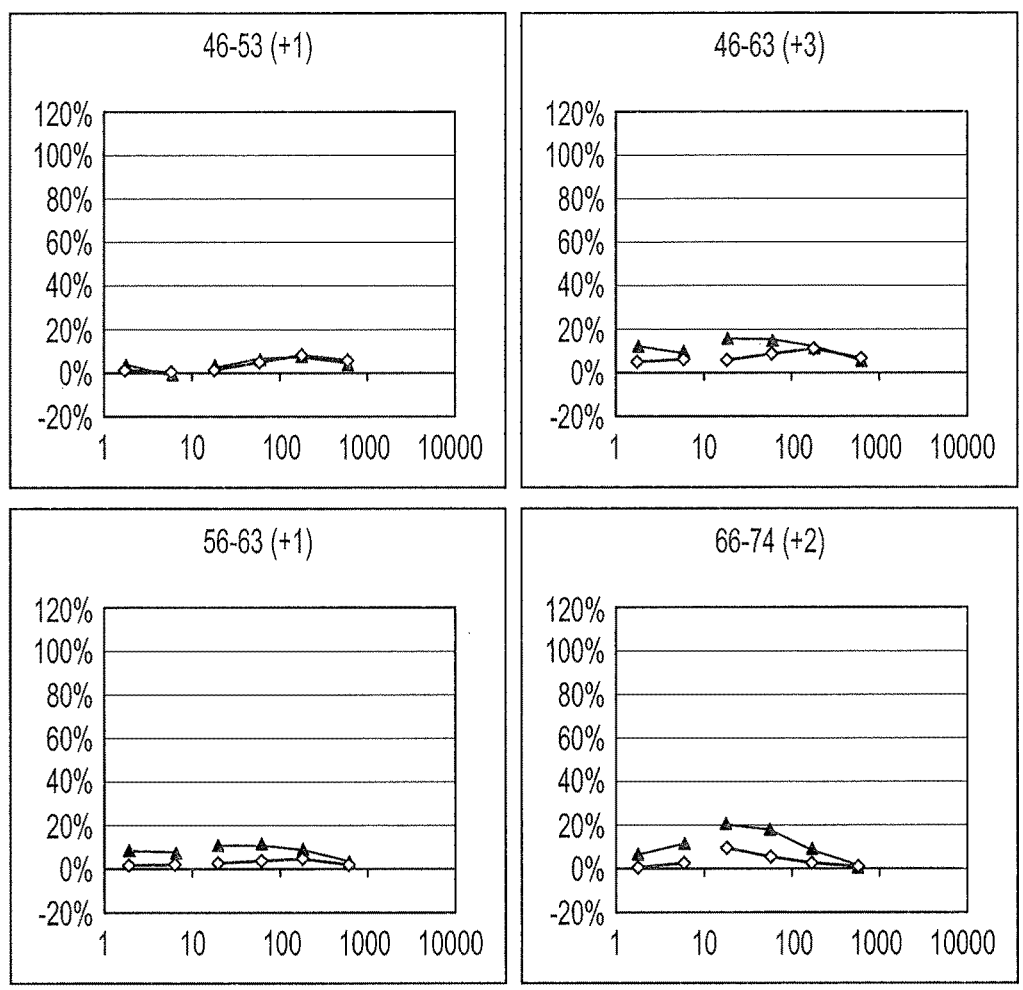
Figure 9D:
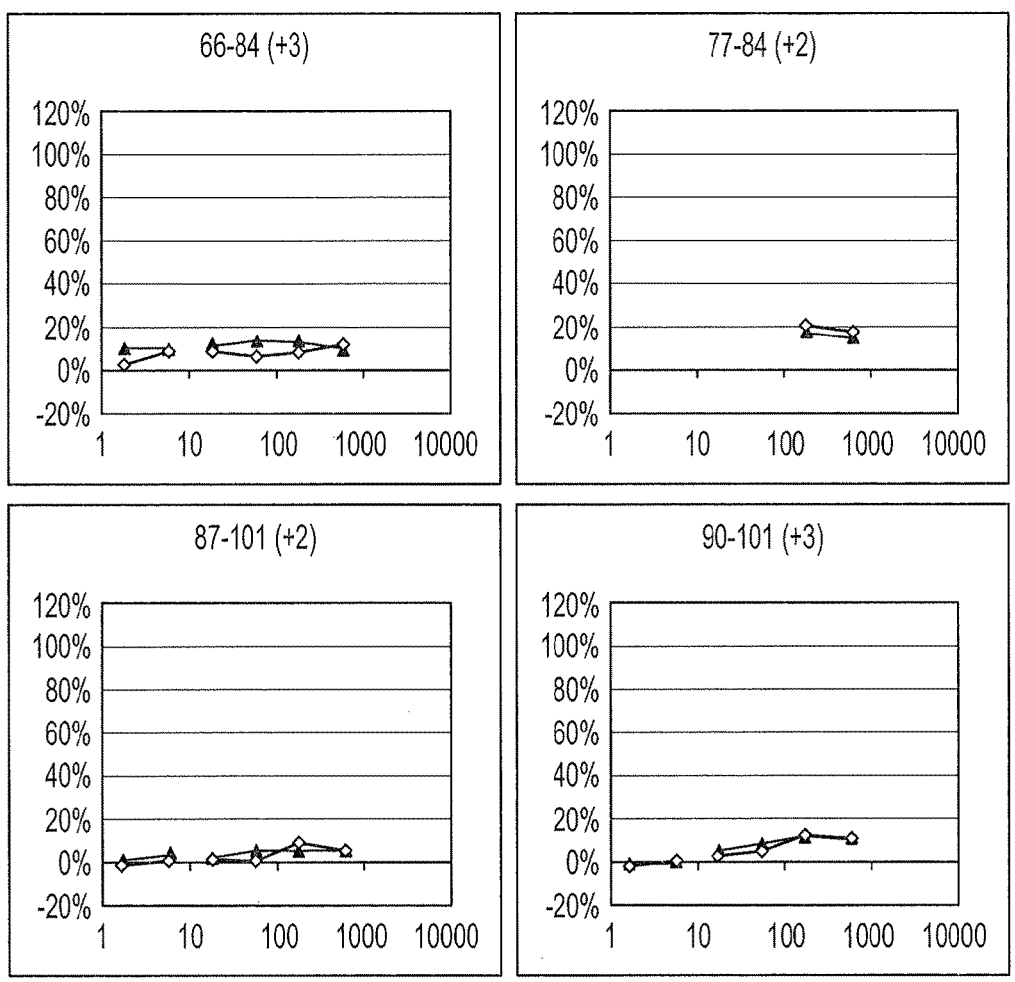
Figure 9E:
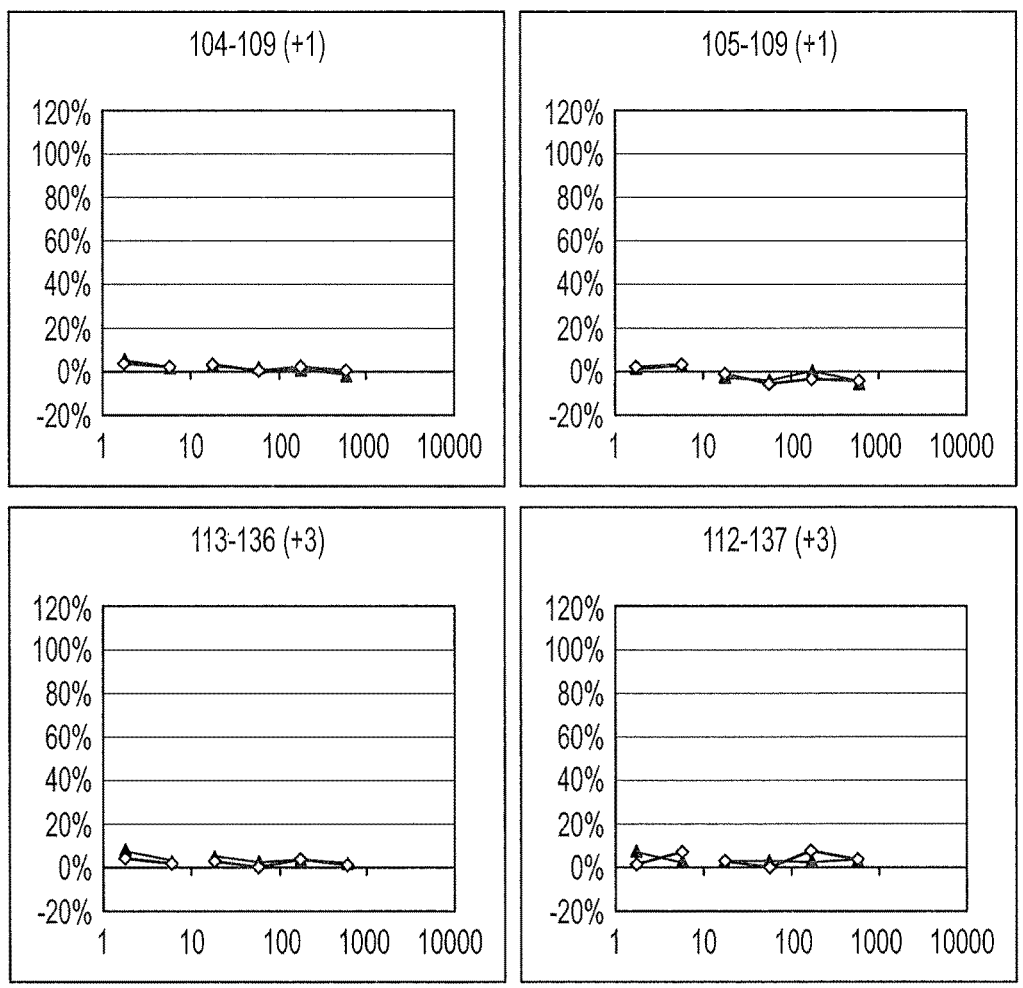
Figure 9F:
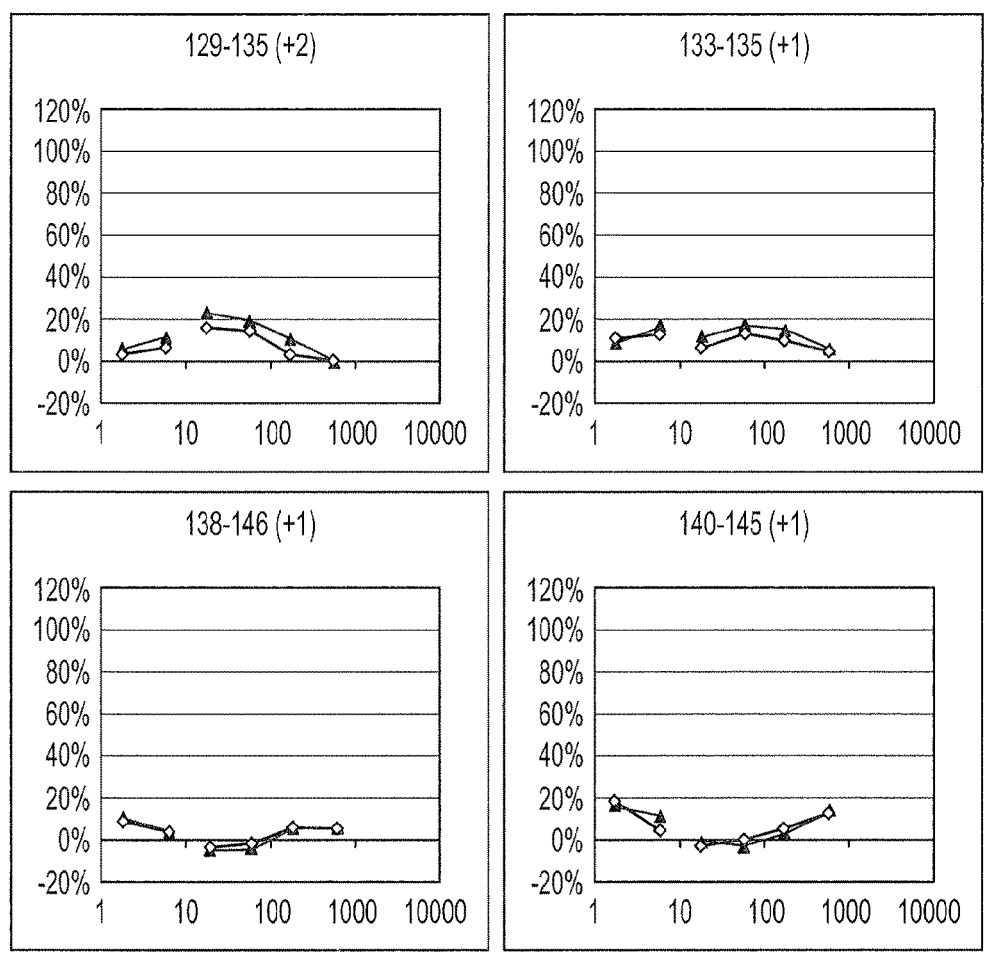

The strongest protections were observed at segments encompassing amino acid residues 56-63 and 66-74 (FIGS. 8A and 9C; Table 2). Analogous segments encompassing amino acid residues 46-63 and 66-84 showed consistent weak protections (FIGS. 8A, 9C and 9D; Table 2). A border line protection was observed for segments encompassing amino acid residues 129-135 (FIGS. 8B, 9E and 9F; Table 2).

TABLE 2

Differences in deuteration levels in various segments of human IL-25 after on/off exchange experiments at pH 7 and pH 8 at 23° C.

| start | end | charge | pH 6 150 | pH 6 500 | pH 7 150 | pH 7 500 | pH 7 1,500 | pH 7 5,000 | average |
|---|---|---|---|---|---|---|---|---|---|
| 3 | 9 | 1 | −3% | 2% | −1% | −1% | −1% | 5% | 0% |
| 3 | 15 | 2 | −3% | −5% | 1% | 0% | −3% | −1% | −2% |
| 3 | 20 | 2 | 1% | 0% | 2% | 1% | −3% | −1% | 0% |
| 12 | 20 | 1 | 0% | 4% | −1% | 0% | 0% | 1% | 1% |
| 23 | 42 | 2 | 3% | 1% | 1% | 0% | −1% | 3% | 1% |
| 23 | 43 | 2 | 3% | 1% | 0% | 0% | −1% | 0% | 0% |
| 23 | 45 | 3 | 2% | 1% | 2% | 1% | 1% | −2% | 1% |
| 23 | 53 | 3 | 2% | 1% | 0% | 1% | 1% | −1% | 1% |
| 46 | 53 | 1 | 2% | −1% | 2% | 1% | 0% | 0% | 1% |
| 46 | 63 | 3 | 8% | 5% | 11% | 7% | 1% | 0% | 5% |
| 56 | 63 | 1 | 7% | 7% | 9% | 8% | 6% | 2% | 6% |
| 66 | 74 | 2 | 6% | 10% | 11% | 13% | 7% | 0% | 8% |
| 66 | 84 | 2 | 9% | 2% | 5% | 7% | 6% | −2% | 4% |
| 77 | 84 | 2 | — | — | — | — | −2% | −2% | −2% |
| 87 | 101 | 2 | 3% | 2% | 1% | 3% | −2% | 1% | 1% |
| 90 | 101 | 2 | 2% | 0% | 3% | 3% | 0% | 1% | 1% |
| 104 | 109 | 1 | 2% | 0% | 0% | 1% | 0% | −2% | 0% |
| 105 | 109 | 1 | 0% | 0% | 0% | 1% | 4% | 0% | 1% |
| 112 | 126 | 2 | 3% | 2% | 3% | 2% | 1% | 0% | 2% |
| 112 | 127 | 2 | 7% | −4% | 1% | 4% | −3% | 1% | 1% |
| 129 | 135 | 2 | 3% | 6% | 8% | 4% | 8% | 0% | 5% |
| 133 | 135 | 1 | −2% | 3% | 7% | 5% | 5% | 2% | 3% |
| 138 | 146 | 1 | 1% | 1% | −1% | −2% | 0% | 1% | 0% |
| 140 | 146 | 1 | −1% | 7% | 3% | −2% | −2% | 2% | 1% |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claim.

What is claimed is:

1. An isolated target binding member that binds IL-25, wherein the target binding comprises an antibody light chain variable region (VL) domain comprising a CDR1 having the amino acid sequence SASQGISNYLN (SEQ ID NO:6) and a CDR2 having the amino acid sequence YTSSLHS (SEQ ID NO:7) and a CDR3 having the amino acid sequence QQYLAFPYTF (SEQ ID NO:8) and an antibody heavy chain variable region (VH) domain comprising a CDR1 having the amino acid sequence GYTMN (SEQ ID NO:10), a CDR2 having the amino acid sequence LINPYNGGTSYNQNFKG (SEQ ID NO:11) and a CDR3 having the amino acid sequence EDYDGYLYFAMDY (SEQ ID NO:12).

2. The target binding member of claim 1, wherein the target binding member binds amino acid residues 56-63 of SEQ ID NO:17 and amino acid residues 66-74 of SEQ ID NO:17.

3. The target binding member of claim 1, wherein the target binding member binds one or more amino acid sequences selected from the group consisting of amino acid residues 46-63 of SEQ ID NO:17 or amino acid residues 66-84 of SEQ ID NO:17.

4. The isolated target binding member of claim 1, wherein the VL domain comprises amino acid residues 1-107 of SEQ ID NO:5.

5. The isolated target binding member of claim 1, wherein the VH domain comprises amino acid residues 1-122 of SEQ ID NO:9.

6. The isolated target binding member of claim 1, wherein the target binding member comprises an antibody constant region.

7. The isolated target binding member of claim 6, wherein the antibody constant region is an IgG1 constant region or an IgG4 constant region.

8. The isolated target binding member of claim 7, wherein the target binding member comprises a whole antibody.

9. The isolated target binding member of claim 1, wherein the target binding member comprises an antibody fragment selected from the group consisting of a Fab antibody fragment, a F(ab')$_2$ antibody fragment, and an scFv antibody fragment.

10. A composition comprising the isolated target binding member of claim 1 and a pharmaceutically acceptable carrier.

11. The composition of claim 10, wherein the composition comprises a lyophilized powder.

12. The isolated target binding member of claim 1, wherein the target binding member has a binding affinity for human IL-25 that is less than or equal to about 50 pM.

13. The isolated target binding member of claim 1, wherein the target binding member comprises a humanized antibody.

* * * * *

SEQUENCE LISTING

<160> NUMBER OF SEQ ID NOS: 26

<210> SEQ ID NO 1
<211> LENGTH: 313
<212> TYPE: DNA
<213> ORGANISM: Homo sapiens

<400> SEQUENCE: 1
gatgacccag tctccatcct ccctgtctgc atctgtagga gacagagtca ccatcacttg      60
cagtgcatcc cagggcatta gcaattatct gaattggtat cagcagaaac agggaaagt     120 tcctaaactc ctgatctatt acacatcaag tttacactca ggggtcccat ctcggttcag    180
cggcagtgga tctgggacag atttcactct caccatcagc agcctgcagc ctgaagatgt    240
tgcaacttat tactgtcagc agtatagcaa gctgccgtac acgtttggcc aggggaccaa    300
gctggagatc aaa                                                       313

<210> SEQ ID NO 2
<211> LENGTH: 107
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Lys Leu Pro Tyr
                85                  90                  95

Thr Phe Gly Gln Gly Thr Lys Leu Glu Ile Lys
            100                 105

<210> SEQ ID NO 3
<211> LENGTH: 363
<212> TYPE: DNA
<213> ORGANISM: Homo sapiens

<400> SEQUENCE: 3
gaggtgcagc tggtcgagag cggagccgag gtgaagaagc caggcgccag cgtcaaggtg      60
tcctgcaagg ccagcggcta cagcttctcc ggctacacca tgaactgggt gcggcaggcc    120
ccaggccaga ggctggaatg gatgggcctg atcaacccct acaacggcgg caccagctac    180
aaccagaact tcaagggcag ggtgacactg accgtggata ccagcgccag caccgcctac    240
ctggaactga acagcctgag aagcgaggac accggcgtgt actactgcgc cagagaggac    300
tacgacggct acctgtactt cgccatggac tactggggcc agggcaccct ggtgaccgtg    360
agc                                                                  363

<210> SEQ ID NO 4
<211> LENGTH: 121
<212> TYPE: PRT
<213> ORGANISM: Homo sapiens

```
<400> SEQUENCE: 4

Glu Val Gln Leu Val Glu Ser Gly Ala Glu Val Lys Lys Pro Gly Ala
  1               5                  10                  15

Ser Val Lys Val Ser Cys Lys Ala Ser Gly Tyr Ser Phe Ser Gly Tyr
             20                  25                  30

Thr Met Asn Trp Val Arg Gln Ala Pro Gly Gln Arg Leu Glu Trp Met
         35                  40                  45

Gly Leu Ile Asn Pro Tyr Asn Gly Gly Thr Ser Tyr Asn Gln Asn Phe
     50                  55                  60

Lys Gly Arg Val Thr Leu Thr Val Asp Thr Ser Ala Ser Thr Ala Tyr
 65                  70                  75                  80

Leu Glu Leu Asn Ser Leu Arg Ser Glu Asp Thr Gly Val Tyr Tyr Cys
                 85                  90                  95

Ala Arg Glu Asp Tyr Asp Gly Tyr Leu Tyr Phe Ala Met Asp Tyr Trp
            100                 105                 110

Gly Gln Gly Thr Leu Val Thr Val Ser
            115                 120

<210> SEQ ID NO 5
<211> LENGTH: 214
<212> TYPE: PRT
<213> ORGANISM: Artificial Sequence
<220> FEATURE:
<223> OTHER INFORMATION: Light chain of antibody I25M6 (M6)

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Ser Ala Ser Gln Gly Ile Ser Asn Tyr
             20                  25                  30

Leu Asn Trp Tyr Gln Gln Lys Pro Gly Lys Val Pro Lys Leu Leu Ile
         35                  40                  45

Tyr Tyr Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Leu Ala Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

-continued

```
<210> SEQ ID NO 6
<211> LENGTH: 11
<212> TYPE: PRT
<213> ORGANISM: Artificial Sequence
<220> FEATURE:
<223> OTHER INFORMATION: LCDR1 of antibody I25M6 (M6)

<400> SEQUENCE: 6

Ser Ala Ser Gln Gly Ile Ser Asn Tyr Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: LCDR2 of antibody I25M6 (M6)

<400> SEQUENCE: 7

Tyr Thr Ser Ser Leu His Ser
1               5

<210> SEQ ID NO 8
<211> LENGTH: 10
<212> TYPE: PRT
<213> ORGANISM: Artificial Sequence
<220> FEATURE:
<223> OTHER INFORMATION: LCDR3 of antibody I25M6 (M6)

<400> SEQUENCE: 8

Gln Gln Tyr Leu Ala Phe Pro Tyr Thr Phe
1               5                   10

<210> SEQ ID NO 9
<211> LENGTH: 452
<212> TYPE: PRT
<213> ORGANISM: Artificial Sequence
<220> FEATURE:
<223> OTHER INFORMATION: Heavy chain of antibody I25M6 (M6)

<400> SEQUENCE: 9

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Thr Met Asn Trp Val Arg Gln Ala Pro Gly Gln Arg Leu Glu Trp Met
        35                  40                  45

Gly Leu Ile Asn Pro Tyr Asn Gly Gly Thr Ser Tyr Asn Gln Asn Phe
    50                  55                  60

Lys Gly Arg Val Thr Leu Thr Val Asp Thr Ser Ala Ser Thr Ala Tyr
65                  70                  75                  80

Leu Glu Leu Asn Ser Leu Arg Ser Glu Asp Thr Gly Val Tyr Tyr Cys
                85                  90                  95

Ala Arg Glu Asp Tyr Asp Gly Tyr Leu Tyr Phe Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

```
                    165                 170                 175
Ala Val Leu Gln Ser Ser Gly Leu Tyr Ser Leu Ser Ser Val Val Thr
                180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 10
<211> LENGTH: 5
<212> TYPE: PRT
<213> ORGANISM: Artificial Sequence
<220> FEATURE:
<223> OTHER INFORMATION: HCDR1 of antibody I25M6 (M6)

<400> SEQUENCE: 10

Gly Tyr Thr Met Asn
 1               5

<210> SEQ ID NO 11
<211> LENGTH: 17
<212> TYPE: PRT
<213> ORGANISM: Artificial Sequence
<220> FEATURE:
<223> OTHER INFORMATION: HCDR2 of antibody I25M6 (M6)

<400> SEQUENCE: 11
```

Leu Ile Asn Pro Tyr Asn Gly Gly Thr Ser Tyr Asn Gln Asn Phe Lys
1               5                   10                  15

Gly

<210> SEQ ID NO 12
<211> LENGTH: 13
<212> TYPE: PRT
<213> ORGANISM: Artificial Sequence
<220> FEATURE:
<223> OTHER INFORMATION: HCDR3 of antibody I25M6 (M6)

<400> SEQUENCE: 12

Glu Asp Tyr Asp Gly Tyr Leu Tyr Phe Ala Met Asp Tyr
1               5                   10

<210> SEQ ID NO 13
<211> LENGTH: 78
<212> TYPE: PRT
<213> ORGANISM: Homo sapiens

<400> SEQUENCE: 13

Met Tyr Ser His Trp Pro Ser Cys Cys Pro Ser Lys Gly Gln Asp Thr
1               5                   10                  15

Ser Glu Glu Leu Leu Arg Trp Ser Thr Val Pro Val Pro Pro Leu Glu
                20                  25                  30

Pro Ala Arg Pro Asn Arg His Pro Glu Ser Cys Arg Ala Ser Glu Asp
            35                  40                  45

Gly Pro Leu Asn Ser Arg Ala Ile Ser Pro Trp Arg Tyr Glu Leu Asp
        50                  55                  60

Arg Asp Leu Asn Arg Leu Pro Gln Asp Leu Tyr His Ala Arg
65                  70                  75

<210> SEQ ID NO 14
<211> LENGTH: 68
<212> TYPE: PRT
<213> ORGANISM: Homo sapiens

<400> SEQUENCE: 14

Cys Leu Cys Pro His Cys Val Ser Leu Gln Thr Gly Ser His Met Asp
1               5                   10                  15

Pro Arg Gly Asn Ser Glu Leu Leu Tyr His Asn Gln Thr Val Phe Tyr
                20                  25                  30

Arg Arg Pro Cys His Gly Glu Lys Gly Thr His Lys Gly Tyr Cys Leu
            35                  40                  45

Glu Ala Arg Leu Tyr Arg Val Ser Leu Ala Cys Val Cys Val Arg Pro
        50                  55                  60

Arg Val Met Gly
65

<210> SEQ ID NO 15
<211> LENGTH: 75
<212> TYPE: PRT
<213> ORGANISM: Homo sapiens

<400> SEQUENCE: 15

Met Tyr Ser His Trp Pro Ser Cys Cys Pro Ser Lys Gly Gln Asp Thr
1               5                   10                  15

Ser Glu Glu Leu Leu Arg Trp Ser Thr Val Pro Val Pro Pro Leu Glu
                20                  25                  30

Pro Ala Arg Pro Asn Arg His Pro Glu Ser Cys Arg Ala Ser Glu Asp

```
                    35                  40                  45

Gly Pro Leu Asn Ser Arg Ala Ile Ser Pro Trp Arg Tyr Glu Leu Asp
 50                  55                  60

Arg Asp Leu Asn Arg Leu Pro Gln Asp Leu Tyr
 65                  70                  75

<210> SEQ ID NO 16
<211> LENGTH: 71
<212> TYPE: PRT
<213> ORGANISM: Homo sapiens

<400> SEQUENCE: 16

His Ala Arg Cys Leu Cys Pro His Cys Val Ser Leu Gln Thr Gly Ser
  1               5                  10                  15

His His Asp Pro Arg Gly Asn Ser Glu Leu Leu Tyr His Asn Gln Thr
                 20                  25                  30

Val Phe Tyr Arg Arg Pro Cys His Gly Glu Lys Gly Thr His Lys Gly
             35                  40                  45

Tyr Cys Leu Glu Arg Arg Leu Tyr Arg Val Ser Leu Ala Cys Val Cys
 50                  55                  60

Val Arg Pro Arg Val Met Gly
 65                  70

<210> SEQ ID NO 17
<211> LENGTH: 146
<212> TYPE: PRT
<213> ORGANISM: Homo sapiens

<400> SEQUENCE: 17

Met Tyr Ser His Trp Pro Ser Cys Cys Pro Ser Lys Gly Gln Asp Thr
  1               5                  10                  15

Ser Glu Glu Leu Leu Arg Trp Ser Thr Val Pro Val Pro Pro Leu Glu
                 20                  25                  30

Pro Ala Arg Pro Asn Arg His Pro Glu Ser Cys Arg Ala Ser Glu Asp
             35                  40                  45

Gly Pro Leu Asn Ser Arg Ala Ile Ser Pro Trp Arg Tyr Glu Leu Asp
 50                  55                  60

Arg Asp Leu Asn Arg Leu Pro Gln Asp Leu Tyr His Ala Arg Cys Leu
 65                  70                  75                  80

Cys Pro His Cys Val Ser Leu Gln Thr Gly Ser His Met Asp Pro Arg
                 85                  90                  95

Gly Asn Ser Glu Leu Leu Tyr His Asn Gln Thr Val Phe Tyr Arg Arg
            100                 105                 110

Pro Cys His Gly Glu Lys Gly Thr His Lys Gly Tyr Cys Leu Glu Arg
            115                 120                 125

Arg Leu Tyr Arg Val Ser Leu Ala Cys Val Cys Val Arg Pro Arg Val
            130                 135                 140

Met Gly
145

<210> SEQ ID NO 18
<211> LENGTH: 11
<212> TYPE: PRT
<213> ORGANISM: Artificial Sequence
<220> FEATURE:
<223> OTHER INFORMATION: LCDR1 of antibody I25M11

<400> SEQUENCE: 18
```

Ser Ala Ser Gln Gly Ile Ala Ser Phe Leu Asn
1               5                   10

<210> SEQ ID NO 19
<211> LENGTH: 11
<212> TYPE: PRT
<213> ORGANISM: Artificial Sequence
<220> FEATURE:
<223> OTHER INFORMATION: LCDR1 of antibody I25M32

<400> SEQUENCE: 19

Ser Ala Ser Gln Gly Ile Asn Glu Tyr Leu Asn
1               5                   10

<210> SEQ ID NO 20
<211> LENGTH: 11
<212> TYPE: PRT
<213> ORGANISM: Artificial Sequence
<220> FEATURE:
<223> OTHER INFORMATION: LCDR1 of antibody I25M30

<400> SEQUENCE: 20

Ser Ala Ser Gln Gly Ile His Trp Asn Leu Asn
1               5                   10

<210> SEQ ID NO 21
<211> LENGTH: 10
<212> TYPE: PRT
<213> ORGANISM: Artificial Sequence
<220> FEATURE:
<223> OTHER INFORMATION: LCDR3 of antibody I25M11

<400> SEQUENCE: 21

Gln Gln Tyr Ser Ser Phe Pro Tyr Thr Phe
1               5                   10

<210> SEQ ID NO 22
<211> LENGTH: 10
<212> TYPE: PRT
<213> ORGANISM: Artificial Sequence
<220> FEATURE:
<223> OTHER INFORMATION: LCDR3 of antibody I25M32 and I25M34

<400> SEQUENCE: 22

Gln Gln Tyr Ile Asn Phe Pro Tyr Thr Phe
1               5                   10

<210> SEQ ID NO 23
<211> LENGTH: 10
<212> TYPE: PRT
<213> ORGANISM: Artificial Sequence
<220> FEATURE:
<223> OTHER INFORMATION: LCDR3 of antibody I25M30

<400> SEQUENCE: 23

Gln Gln Phe Asn Ser Phe Pro Tyr Thr Phe
1               5                   10

<210> SEQ ID NO 24
<211> LENGTH: 13
<212> TYPE: PRT
<213> ORGANISM: Artificial Sequence
<220> FEATURE:
<223> OTHER INFORMATION: HCDR3 of antibody I25M10 adn I25M11

<400> SEQUENCE: 24

Glu Asp Phe Asp Ser Trp Thr Phe Phe Ala Met Asp Tyr

```
<210> SEQ ID NO 25
<211> LENGTH: 13
<212> TYPE: PRT
<213> ORGANISM: Artificial Sequence
<220> FEATURE:
<223> OTHER INFORMATION: HCDR3 of antibody I25M20, I25M32

<400> SEQUENCE: 25

Glu Asp Tyr Asp Ser Trp Thr Phe Phe Ala Met Asp Tyr
1               5                   10

<210> SEQ ID NO 26
<211> LENGTH: 13
<212> TYPE: PRT
<213> ORGANISM: Artificial Sequence
<220> FEATURE:
<223> OTHER INFORMATION: HCDR3 of antibody I25M28, I25M30, I25M31,
      I25M34

<400> SEQUENCE: 26

Glu Asp Phe Asp Ser Trp Thr Tyr Phe Ala Met Asp Tyr
1               5                   10
```